United States Patent
Tayebi et al.

(10) Patent No.: US 9,354,195 B2
(45) Date of Patent: May 31, 2016

(54) HIGHLY SELECTIVE COATED-ELECTRODE NANOGAP TRANSDUCERS FOR THE DETECTION OF REDOX MOLECULES

(71) Applicants: Noureddine Tayebi, Menlo Park, CA (US); Xing Su, Cupertino, CA (US); Handong Li, Santa Clara, CA (US)

(72) Inventors: Noureddine Tayebi, Menlo Park, CA (US); Xing Su, Cupertino, CA (US); Handong Li, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 159 days.

(21) Appl. No.: 14/104,546

(22) Filed: Dec. 12, 2013

(65) Prior Publication Data

US 2015/0168341 A1 Jun. 18, 2015

(51) Int. Cl.
*G01N 27/327* (2006.01)

(52) U.S. Cl.
CPC ........................ *G01N 27/3278* (2013.01)

(58) Field of Classification Search
CPC .................................................... G01N 27/327
See application file for complete search history.

(56) References Cited

U.S. PATENT DOCUMENTS

| | | | | |
|---|---|---|---|---|
| 2008/0149479 A1* | 6/2008 | Olofsson | ................ | B82Y 15/00 204/403.14 |
| 2008/0229831 A1* | 9/2008 | Serban et al. | ................... | 73/589 |
| 2009/0032401 A1* | 2/2009 | Ronaghi | ........... | B01L 3/502761 204/549 |
| 2011/0056845 A1 | 3/2011 | Stellacci et al. | | |
| 2011/0155586 A1 | 6/2011 | Elibol et al. | | |
| 2012/0253340 A1* | 10/2012 | Stevenson | ............ | H03H 7/0123 606/33 |
| 2013/0001082 A1 | 1/2013 | Afzali-Ardakani et al. | | |
| 2013/0334402 A1* | 12/2013 | Izuha | .................... | H01L 27/146 250/208.1 |
| 2015/0131139 A1* | 5/2015 | Tsukamoto | .......... | G02B 5/1828 359/266 |

FOREIGN PATENT DOCUMENTS

| | | | |
|---|---|---|---|
| JP | 2013-048221 | * | 3/2013 |
| JP | 2012-099135 | * | 4/2013 |
| WO | WO-2013100949 | | 7/2013 |

OTHER PUBLICATIONS

Ripert et al. (Electrochimica Acta 91 (2013) 82-89).*
Leipold et al. (Anal Bioanal Chem (2008) 391:1759-1772).*
Eid, John, et al., "Real-Time DNA Sequencing from Single Polymerase Molecules", www.sciencemag.org, vol. 323, Jan. 2, 2009, 6 pgs.
Fuller, Carl W., et al., "The challenges of sequencing by synthesis", Nature biotechnology, vol. 27, No. 11, Nov. 2009, 11 pgs.
Gupta, Amar P., et al., "The effect of the 3', 5' thiophosphoryl linkage on the exonuclease of T4 polymerase and the Klenow fragment", Nucleic Acids Research, vol. 12, No. 14, Jun. 1984, 15 pgs.
Knorre, Dmitri G., et al., "General Method for the Synthesis of ATP Gamma-Derivatives", FEBS Letters, vol. 70, No. 1, Nov. 1976, 4 pgs.

(Continued)

*Primary Examiner* — Jennifer Dieterle
(74) *Attorney, Agent, or Firm* — Blakely, Sokoloff, Taylor & Zafman LLP

(57) ABSTRACT

Highly selective coated-electrode nanogap transducers for the detection of redox molecules are described. In an example, an analyte detection system includes one or more transducer electrodes having a surface for analyte detection. The surface includes a coating to inhibit direct contact of analyte with the surface of the one or more transducer electrodes.

6 Claims, 16 Drawing Sheets

(56) References Cited

OTHER PUBLICATIONS

Korlach, Jonas, et al., "Long, Processive Enzymatic DNA Synthesis Using 100% Dye-Labeled Terminal Phosphate-Linked Nucleotides", Nucleosides, Nucleotides and Nucleic Acids, vol. 27, No. 9, URL:http://dx.doi.org/10.1080/15257770802260741, 13 pgs.

Margulies, Marcel, et al., "Genome sequencing in microfabricated high-density picolitre reactors", Nature, vol. 437, Sep. 15, 2005, doi:10.1038/nature03959, 6 pgs.

Yang, Zunyi, et al., "Nucleoside alpha-thiotriphosphates, polymerases and the exonuclease III analysis of oligonucleothides containing phosphorothioate linkages", Nucleic Acids Research, vol. 35, No. 9, Apr. 2007, doi:10.1093/nar/gkm168, 10 pgs.

International Search Report and Written Opinion from PCT/US2014/060474 mailed Jan. 22, 2015, 13 pgs.

Mahapatro, et al., "Electronic Transport through Ruthenium-Based Redox-Active Molecules in Metal-Molecule-Metal Nanogap Junctions," Nano Letters, Jun. 27, 2008, vol. 8, No. 8, pp. 2131-2136.

\* cited by examiner

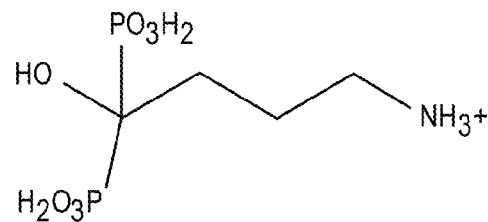 Positive (802)
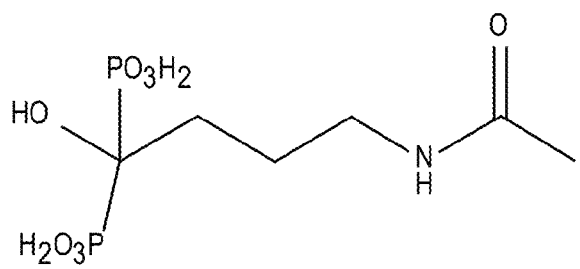 Neutral (804)
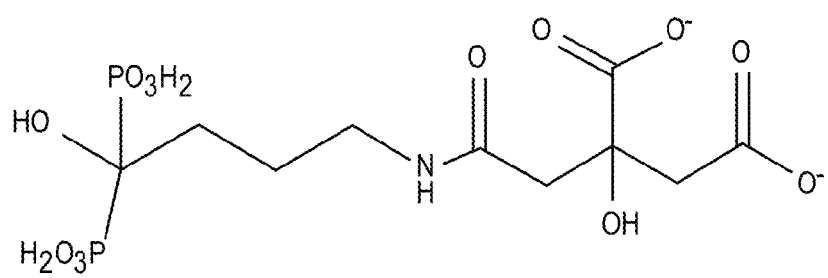 Negative (806)
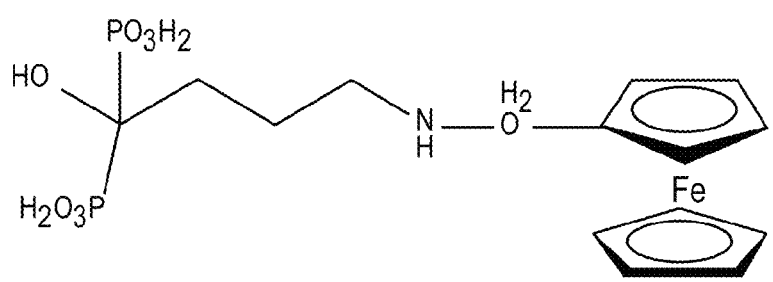 Mediating (808)
FIG. 8

HIGHLY SELECTIVE COATED-ELECTRODE NANOGAP TRANSDUCERS FOR THE DETECTION OF REDOX MOLECULES

TECHNICAL FIELD

Embodiments of the invention are in the field of devices and methods for detection of biomolecules such as analytes and, in particular, highly selective coated-electrode nanogap transducers for the detection of redox molecules.

BACKGROUND

DNA sequencing is in the throes of an enormous technological shift marked by dramatic throughput increases, a precipitously dropping per-base cost of raw sequence, and an accompanying requirement for substantial investment in large capital equipment in order to utilize the technology. Investigations that were, for most, unreachable luxuries just a few years ago (individual genome sequencing, metagenomics studies, and the sequencing of myriad organisms of interest) are being increasingly enabled, at a rapid pace.

Genetic information in living organisms is contained in the form of very long nucleic acid molecules such as deoxyribonucleic acid (DNA) and ribonucleic acid (RNA). Naturally occurring DNA and RNA molecules are typically composed of chemical building blocks called nucleotides, bound together by a phosphate backbone, which are in turn made up of a sugar (deoxyribose or ribose, respectively), and one of four bases, adenine (A), cytosine (C), guanine (G), and thymine (T) or uracil (U). The human genome, for example, contains approximately three billion nucleotides of DNA sequence and an estimated 20,000 genes. DNA sequence information can be used to determine multiple characteristics of an individual as well as the presence of or susceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes or sections of the genome of individuals provides an opportunity to personalize medical treatments. The need for nucleic acid sequence information also exists in research, environmental protection, food safety, biodefense, and clinical applications, such as for example, pathogen detection, i.e., the detection of the presence or absence of pathogens or their genetic variants.

Thus, because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as, for example, those containing 1-20 bases performed with specific primers. Sequencing methods that provide increased accuracy and or robustness, decreased cost, reduced input sample, and or high throughput are valuable analytical and biomedical tools.

Additionally, molecular detection platforms that have a reduced capital cost, are miniaturized and manufacturable in high volumes provide access to affordable disease detection to many people in places and situations in which such access was not in the past possible. The availability of affordable molecular diagnostic devices reduces the cost of and improves the quality of healthcare available to society. Additionally, portable molecular detection devices have applications in security and hazard detection and remediation fields and offer the ability to immediately respond appropriately to a perceived security or accidental biological or chemical hazard.

However, many improvements are still needed in the area of DNA sequencing and DNA sequencing detection.

BRIEF DESCRIPTION OF THE DRAWINGS

FIG. 8 illustrates alendronate derivatives suitable for organic coatings, in accordance with an embodiment of the present invention.

DESCRIPTION OF THE EMBODIMENTS

Figure 1:
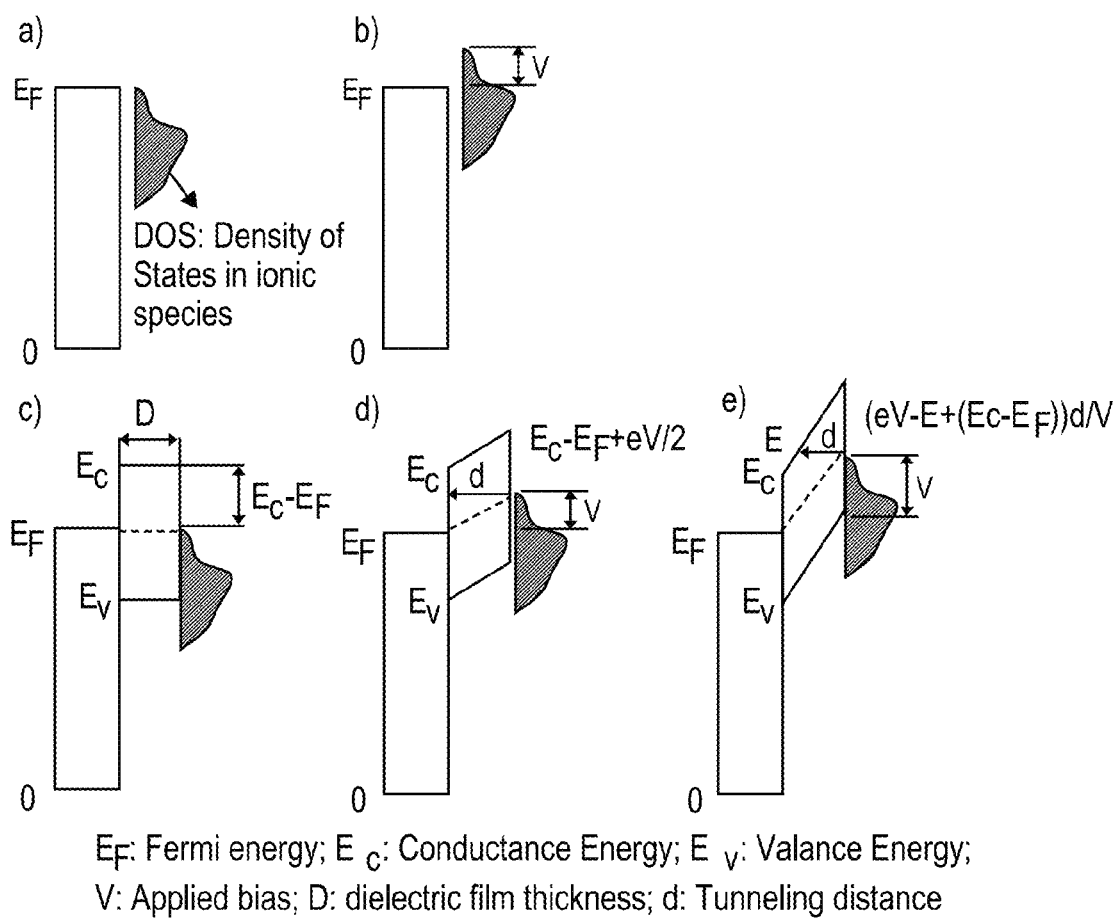
FIG. 1 illustrates (a) a band diagram at the electrode-redox molecule interface in equilibrium without bias, (b) when a bias is applied, (c) potential configuration at oxide coated electrode without bias, (d) when $eV<E_C-E_F=E_0$, and (e) when $eV>E_C-E_F=E_0$, in accordance with an embodiment of the present invention.

Highly selective coated-electrode nanogap transducers for the detection of redox molecules are described. In the following description, numerous specific details are set forth, such as detection approaches, in order to provide a thorough understanding of embodiments of the present invention. It will be apparent to one skilled in the art that embodiments of the present invention may be practiced without these specific details. In other instances, well-known features, such as integrated circuit design layouts, are not described in detail in order to not unnecessarily obscure embodiments of the present invention. Furthermore, it is to be understood that the various embodiments shown in the Figures are illustrative representations and are not necessarily drawn to scale.

One or more embodiments are targeted to DNA sequencing using electrical detection technology. Embodiments may address approaches for providing a compact DNA sequencing platform suitable to perform highly sensitive signal detection in a highly parallel fashion. Furthermore, one or more embodiments provide a cost effective and accurate sequencing system to enable wide applications of genomic information for the improvement of human health. To provide context, conventional DNA sequencing technology can be used to decode an individual's genomic DNA sequence of over 3 billion base pairs. However, the total cost of DNA sequencing remains prohibitive at least in part due to complex instrumentation and costly consumables. For routine biomedical analyses, a DNA sequencing platform needs to be compact, sensitive, accurate and exhibit high throughput such that the overall cost is affordable.

The ability to detect biomolecules at ultra-low concentrations has the potential to revolutionize several fields including disease detection/treatment and environmental screening/monitoring. Manufacturing electronic biochemical sensors with high sensitivity and the potential for massively parallel scaling will allow the realization of highly affordable, customizable, and miniaturized systems for such applications including DNA sequencing platforms, in accordance with an embodiment of the present invention.

One or more embodiments described herein are directed to the design and manufacturing of a high sensitivity sensor which can detect reaction product(s) from biochemical reactions involving single molecules using redox cycling-based detection. Such embodiments may be implemented to significantly improve the signal to noise ratio in a transduction scheme used in DNA sequencing platforms for signal transduction, which involves detection of a redox-active molecule using redox cycling in nanogap transducers. As such, improved sensitivity in detection of DNA may be achieved, pushing towards single-molecule detection.

To provide further context, it is to be appreciated that a number of problems may be associated with existing redox cycling transducers, which utilize platinum as an electrode material. First, a resulting catalytic effect of metal on redox tag degradation can lower signal level. Second, high background current can mask the actual signal to be detected (i.e., providing high noise). Third, adsorption of detected species on electrodes can result in lowering the total signal level (i.e., resulting in low signal). Fourth, the operation potential may be limited depending on the electrode properties interacting with the background (e.g., limited redox species that can be used as a tag, minimizing the optimization window and ultimately decreasing the optimal signal level). Noble metals (e.g., Pt, Au, Ag) are typically used as electrodes for redox measurements because of their chemical stability. However, their chemical catalytic properties can also be adverse to measurement sensitivity and accuracy because organic analytes and water molecules that are in direct contact with the metal atoms can undergo molecular conversion or electrolysis more easily. Such a catalytic effect may result in high background current and analyte degradation. One or more embodiments described herein provide solutions to reduce the above described catalytic effect.

Past approaches to addressing the above issues have partially reduced these problems by using diamond, which possesses better electrochemical properties. However, diamond is usually deposited at high temperatures that are not CMOS-compatible. In a first aspect, in accordance with an embodiment of the present invention, a transducer electrode material (e.g., platinum or any other electrochemically active material such as diamond, gold, ITO, Iridium oxide, etc) is coated with a very thin (e.g., between 0 to 7 nm thick) dielectric film (e.g., $Ta_2O_5$, $TiO_2$, $SiO_2$, $Y_2O_3$, $Al_2O_3$, $HfO_2$, $ZrO_2$, $ZrSiO_4$, $BaTiO_3$, $BaZrO_3$, $Si_3N_4$, etc.), to prevent or reduce any catalytic reaction of the transducer material with solution additives. Furthermore, such coating may be performed to reduce adsorption, without significantly affecting the electron transfer at the reducing and oxidizing electrodes. In one embodiment, the dielectric film coating possesses a low energy barrier (see FIGS. 1 and 2) to enable electron tunneling or hopping through or over the energy barrier to maintain a similar electron transfer rate as compared with bare electrodes. In another embodiment, thin conductive materials that are non-catalytic and non-electrochemically/electrochemically active can also be used as protective films on electrochemically active films or on a combination of electrochemically active films.

In an embodiment, a method for reliably fabricating a redox cycling sensor in a CMOS compatible manner is provided, allowing dense integration on a single platform. Such a redox cycling sensor can be as described in US patent publication 2011/0155586 filed Dec. 31, 2009 and entitled, "*Nanogap chemical and biochemical sensors*," which is incorporated by reference herein. Embodiments described herein may include similar or the same devices but may have the added feature of depositing a very thin (e.g., between approximately 0 to approximately 7 nm thick) dielectric film on both the bottom and top electrode material. Such devices may be used to maximize a signal to noise ratio for the detection of any molecule that can go through reversible (or quasi reversible, since depending on the detection scheme short lifetime reactions can also be detected) redox reactions. In an embodiment, the same or similar coating scheme can also be used on transducers that possess one working electrode whereby cycling is accomplished chemically instead of electrically, as is the case for the nanogap transducer scheme.

To provide further context, in the case of DNA sequencing, a biochemical assay system (reaction) has been designed so that nucleotide base specific redox tags are activated between two electrodes separated by a nanogap (e.g., a gap of 50 nm or less). A third reference electrode may be used to fix the bias of the fluid. The presence of the active redox tags are detected by monitoring either one of the two electrode currents. Having two closely spaced electrodes biased close to the reduction and oxidation potentials of the redox tag allows signal amplification because the same molecule carries electrons from the oxidation electrode to the reduction electrode through the gap between these electrodes multiple times. Placing the electrodes closer to each other results in higher signal because it decreases the diffusion time of the redox tag from one electrode to another. The amount of current registered is proportional to the number of non-adsorbed molecules in the gap. In accordance with an embodiment of the present invention, coating the electrode material with a thin dielectric film in such a nanogap redox cycling architecture provides for higher signal to noise ratio. Such an implementation can allow the readout circuitry to discriminate the redox current due to the redox tag with minimum background current contribution from the buffer. Furthermore, the material architecture can present an inert surface, minimizing adsorption of molecules so more of the molecules can keep shuttling more electrons resulting in more signal. Thus, embodiments described herein can be based on an understanding of tunneling and hopping theories behind electron transfer at the dielectric redox molecule interface, and methods to fabricate nanogap devices with such coatings are thus outlined. Designs described herein may utilize a minimum number of fabrication operations, decreasing the manufacturing cost and improving the yield.

As a comparison, state-of-the art nanogap sensor electrodes are fabricated to have bare electrochemically-active electrodes (e.g., conductive materials such as platinum, diamond, gold, ITO, iridium oxide, etc.). With such electrodes, problems outlined above have been addressed by one or more of the following: (1) operating the device at electrode potentials in which the background is minimal, (2) using electrode surface modifications to minimize adsorption on surfaces, (3) using optimized electrolyte or buffer conditions to minimize adsorption on surfaces, (4) using increased concentrations of analyte to get more signal from the devices, (5) alternatively, if the analyte tends to polymerize on the surface, using reduced concentrations of analyte to reduce the rate of electrode fouling, or (6) choosing redox compounds that are within the operational range of the devices defined by the potential scanning window of the used electrode materials. However, such procedures have proven very complex, time consuming and do not necessarily produce repeatable results, thereby reducing reliability and repeatability.

Thus, as touched on above, in a first aspect, embodiments are directed to coating, and thus protecting, transducer electrode material (e.g., platinum or any other electrochemically active material such as diamond, gold, ITO, iridium oxide, etc.) with a very thin (e.g., approximately in the range of 0 to 7 nm thick) dielectric film (e.g., $Ta_2O_5$, $TiO_2$, $SiO_2$, $Y_2O_3$, $Al_2O_3$, $HfO_2$, $ZrO_2$, $ZrSiO_4$, $BaTiO_3$, $BaZrO_3$, $Si_3N_4$, etc), to reduce or altogether prevent catalytic reaction of the transducer material with solution additives and to reduce the effect of adsorbed species, without significantly affecting the electron transfer at the reducing and oxidizing electrodes. As mentioned above, the dielectric film should possess a low energy barrier to enable electron tunneling or hopping through or over the energy barrier to maintain a similar electron transfer rate as with bare electrodes. Thin conductive materials (e.g., Ru) that are non-catalytic and non-electrochemically active can also be used as protective films. By doing so, in an embodiment, the above state-of-the art solutions need not be implemented thereby reducing complexity, increasing yield and producing reliable and repeatable results. Moreover, embodiments described herein allow for the option to operate at a wider range of electrode potentials, increasing the options for redox tags. Increasing redox tag options allows for the optimization of the tag molecules for maximum signal. In addition, the developed process is scalable such that semiconductor manufacturing scalability can be exploited to reduce the size of the sensor. Finally, the same or similar coating scheme can also be used on transducers that possess one electrode (excluding a reference electrode) whereby cycling is accomplished chemically instead of electrically as it is the case for the nanogap transducer scheme.

Thus, embodiments described herein can provide a scalable and integratable manufacturing process for producing redox sensors. Moreover, development of the theory behind previous solutions described above has provided the opportunity to tune the parameters that can provide the best sensitivity. In particular, allowing the selection of optimal electrode coatings. In one or more embodiments of the present invention, as described below, theory along with a combination of state-of-the art devices integrated with new materials and processing operations enables the use of, and benefit of, electrode coating materials.

FIG. 1 illustrates (a) a band diagram at the electrode-redox molecule interface in equilibrium, (b) when a bias is applied, (c) potential configuration at oxide coated electrode without bias, (d) when $eV<E_C-E_F=E_0$, and (e) when $eV>E_C-E_F=E_0$, in accordance with an embodiment of the present invention.

Referring to part (a) of FIG. 1, as shown schematically, under equilibrium conditions (i.e., no applied bias), the effective electronic densities of states of the reduced and oxidized ionic species in contact with the electrode surface are provided. The effective electronic densities of states are most properly considered as the relative probability, in a redox process, of adding an electron of a given energy to the oxidized species or removing an electron of a given energy from the reduced species. Near the Fermi level, an exponential approximation is often considered. When a bias V (part (b) of FIG. 1) is applied, it leads to a net electronic current from the reduced species to the electrode (or from the oxidized species to the electrode). In an embodiment, the electrodes are coated with a thin dielectric through which the electron tunnels or hops over an effective energy barrier (part (c) of FIG. 1).

In the case that $eV<E_C-E_F=E_0$ (part (d) of FIG. 1), the current associated with the electron transfer rate through tunneling is given by equation (1):

$$I(V) = \int_0^{-E_F+V} \frac{qy(E)\exp\left(\frac{-2^{E/2}D\sqrt{m}/h}{\left(E_{o+}\frac{1}{2}qV + E_F - E\right)^{\frac{1}{2}}}\right) DOS(E-qV)dE}{\exp((E_F-E)/kT)+1} \quad (1)$$

In the case that $eV>E_C-E_F$ (part (e) of FIG. 1), the current consists of two contributions: electrons with energy less and greater than $E_V-E_0$. The current generated from electrons with energy less than $E_V-E_0$ is the same as equation (1), whereas the current generated from electrons with energy greater than $E_V-E_0$ is given by equation (2):

$$I(V) = \int_0^{-E_F+E_0} \frac{qy(E)\exp\left(\frac{-2^{\frac{3}{2}}D\sqrt{m}}{h}\right) DOS(E-qV)dE}{\left(E_{0+}\frac{1}{2}qV+E_F-E\right)^{\frac{1}{2}}} + \int_{-E_F+E_0}^{-E_F+qV_0} \frac{qy(E)\exp\left(\left(\frac{2^{\frac{3}{2}}D\sqrt{m}}{h}\right)(E_{u+}qVE_F-E)^{\frac{1}{2}}\right) DOS(E-qV)dE}{\sqrt{2}\,qV\exp\left(\frac{(E_F-E)}{kT}\right)+1} \quad (2)$$

Ideally, operation should be in the $eV>E_C-E_F$ case to maximize the electron transfer rate while reducing the applied bias V. To do so, however, in an embodiment, dielectrics with low energy barriers are used. Thinner films should also be deposited to reduce the tunneling distance but a compromise needs to be struck between film thicknesses and reduced electrode-catalytic activity and fouling.

Figure 2:
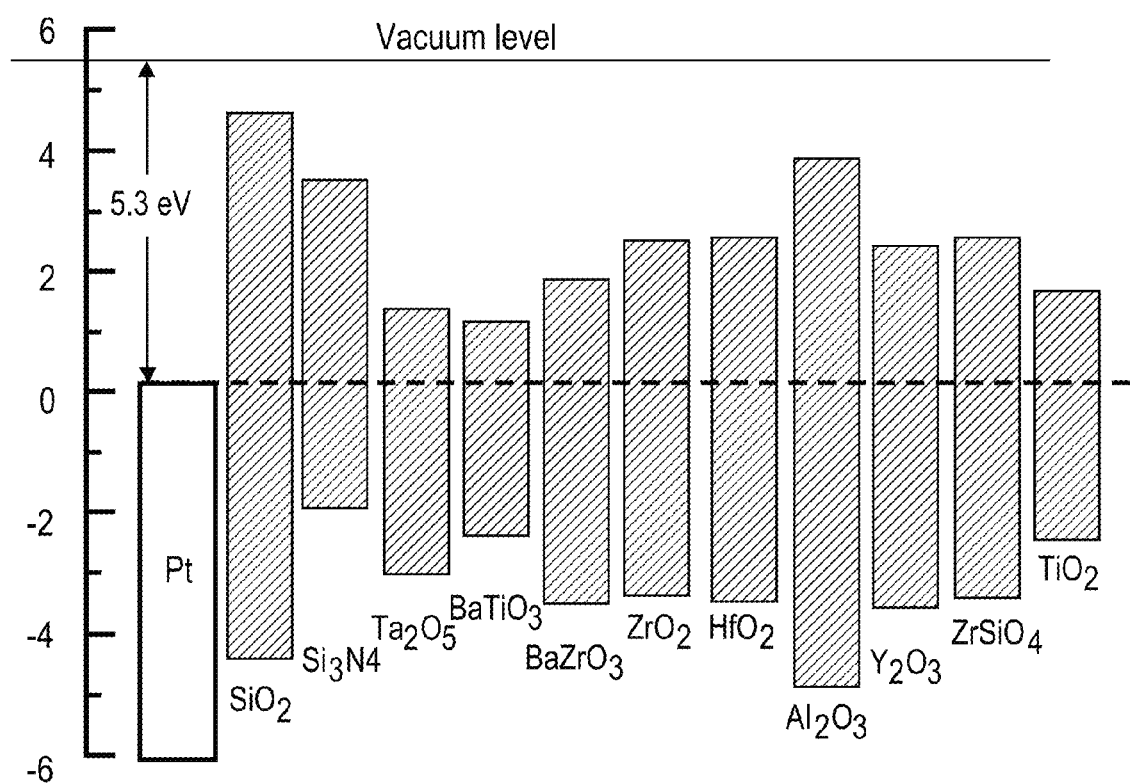
FIG. 2 is a plot showing a comparison of band energy levels of potential protective dielectric films and their position with respect to the platinum work function, which defines the energy barrier.

FIG. 2 is a plot 200 showing a comparison of energy band levels of potential protective dielectric films and their position with respect to platinum work function, which defines the energy barrier. Referring to FIG. 2, various dielectric films are demonstrated as compared to a platinum electrode. It is to be appreciated that the list of 11 dielectric films in plot 200 is not restrictive and may be extended to any other dielectric material. The same is applied to electrode material that can be any electrochemically active material. Moreover, thin conductive materials that are non-catalytic and non-electrochemically active can also be used as protective films. Finally, it is to be appreciated that operating at higher temperatures can spread the electronic density of states, and increase the electron energy which will in turn increase the electron tunneling and hopping probabilities, thereby increasing the electron transfer rate.

In accordance with an embodiment of the present invention, a new fabrication process is described for incorporating a protective dielectric film (or conductive film that is non-catalytic and non-electrochemically active), such as those described above, which consists of depositing a thin (e.g., between approximately 0-7 nm thick) film using atomic layer deposition (or any other deposition procedure such as sputtering, evaporation, etc). The resulting fabricated transducer may be utilized for DNA sequencing. The resulting transducer may also be utilized for enzymatically tagged assays. More generally, one or more embodiments described herein provide a unique combination of using protective coatings on electrodes with a nanogap architecture for redox cycling detection of molecules.

Figure 3:
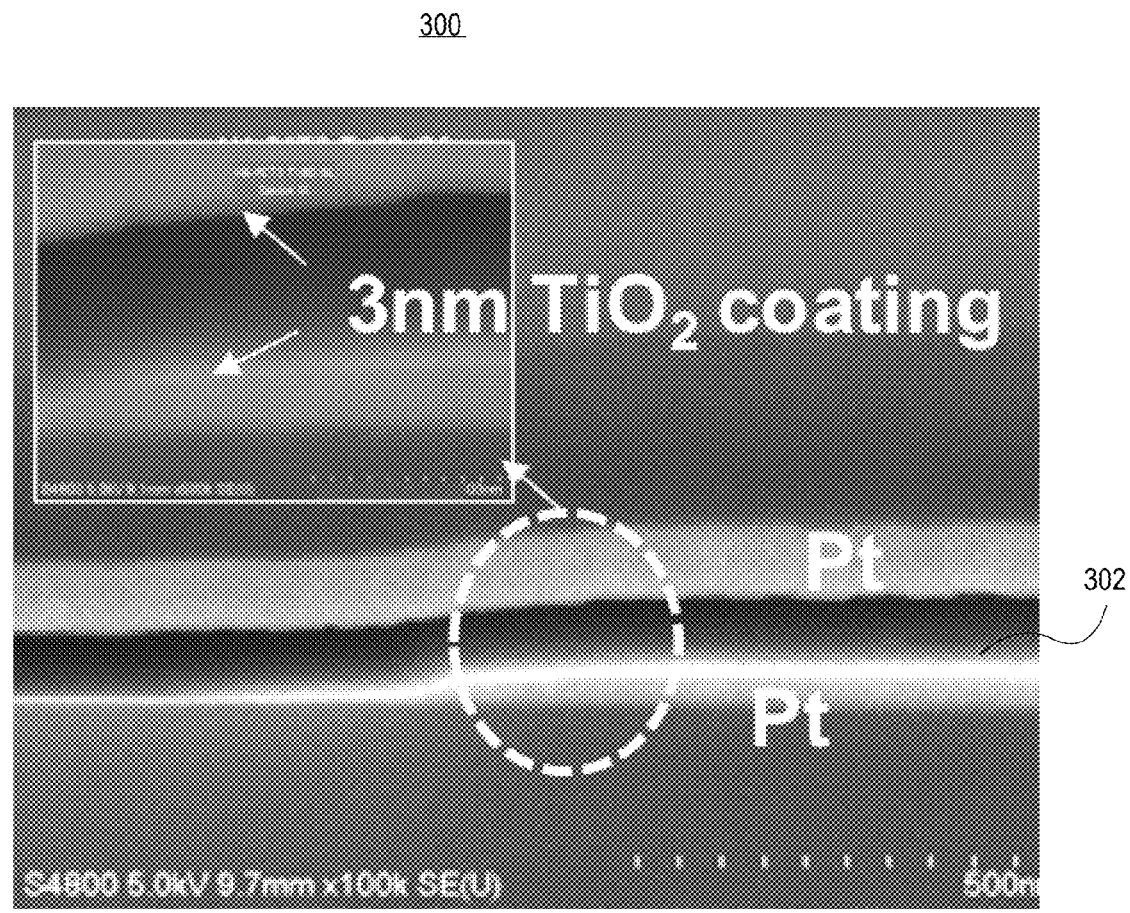
FIG. 3 is a cross-sectional scanning electron micrograph of a nanogap device showing 3 nm thick $TiO_2$ coating layers on platinum electrodes, in accordance with an embodiment of the present invention.

FIG. 3 is a cross-sectional scanning electron micrograph 300 of a nanogap device showing 3 nm thick $TiO_2$ coating layers on platinum electrodes, in accordance with an embodiment of the present invention. Referring to FIG. 3, a sacrificial layer, which can selectively be etched such as chromium, tungsten, etc., was etched to provide a approximately 50 nm gap 302 between the electrodes.

Figure 4:
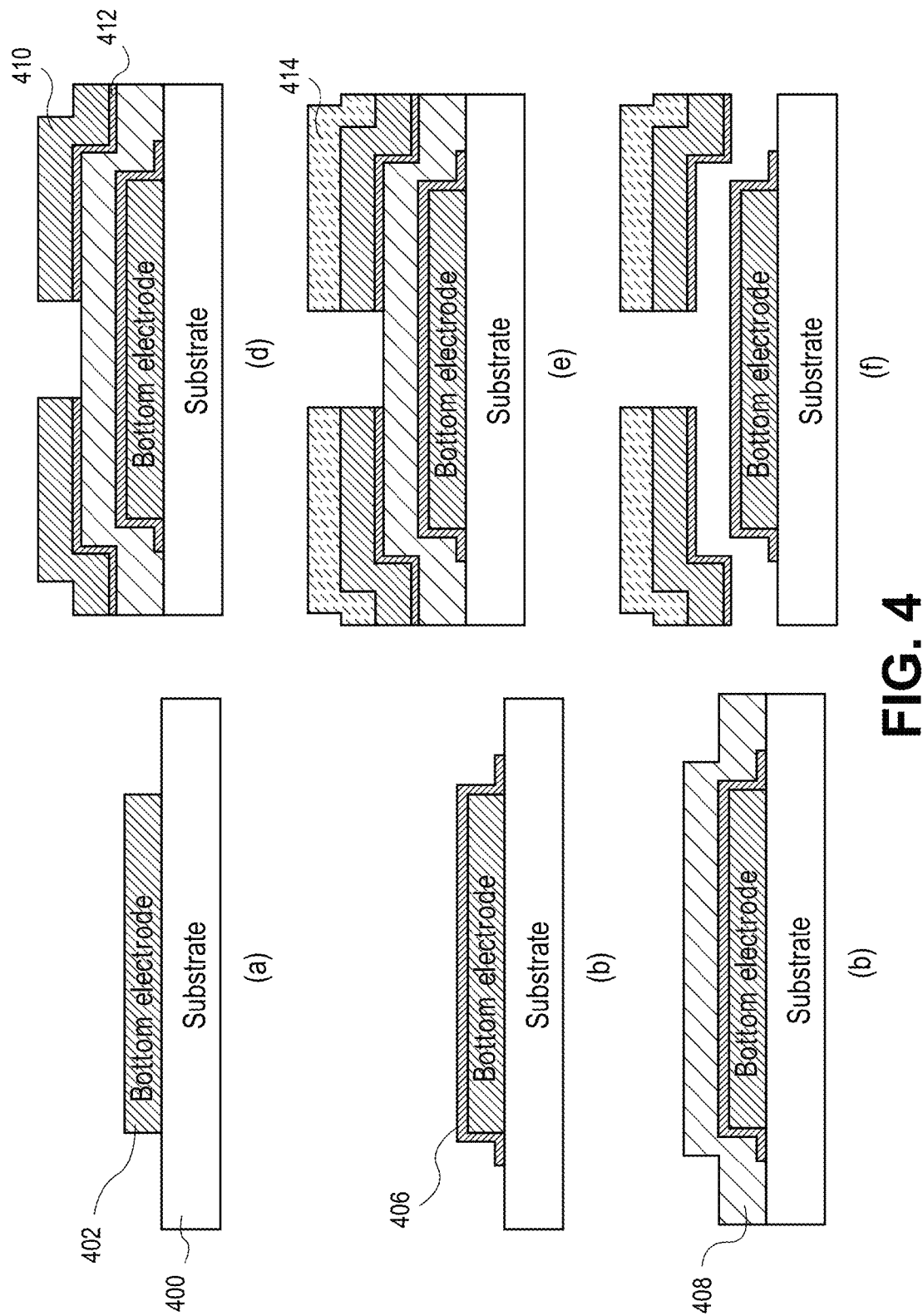
FIG. 4 illustrates cross-sectional views representing various operations in a method of fabricating a nanogap transducer device with protective coatings, in accordance with an embodiment of the present invention.

FIG. 4 illustrates cross-sectional views representing various operations in a method of fabricating a nanogap transducer device with protective coatings, in accordance with an embodiment of the present invention.

Referring to part (a) of FIG. 4, a bottom electrode 402 is formed on or above a substrate 400. In one embodiment, the bottom electrode 402 is fabricated via a material deposition, lithography, hardmask deposition, and etching processing scheme. In one embodiment, the bottom electrode 402 is formed to have minimal surface roughness and with minimal thickness in order to minimize the probability of later shorting of the top and bottom electrodes. Roughness may cause openings in the sacrificial conformal coating and edges with high aspect ratios may cause thinning/voids in the sacrificial layer. In one embodiment, the bottom electrode 402 is composed of a material such as, but not limited to, platinum, gold, diamond, ITO or iridium oxide, and is deposited with a technique such as, but not limited to, evaporation, sputtering, ALD, CVD or hot filament. In the case of diamond, a thick film may need to be deposited and high aspect ratio structures at the edges of the electrodes may be formed. Such high aspect ratio structures may lead to thinning of the sacrificial film at the edges of the electrodes, increasing the probability of shorting between the top and bottom electrodes. To mitigate such issues, in one embodiment, the nanogap devices may be planarized by depositing a dielectric layer (e.g., silicon nitride or silicon dioxide) and using chemical mechanical polishing (CMP) of the dielectric to achieve a planar surface for subsequent enhanced conformal coating of the following layers. In some embodiments, an adhesion layer such as chromium, tantalum, or various other adhesion layers may be utilized to improve bonding between the electrode and the substrate.

Referring to part (b) of FIG. 4, a protective film 406 is then formed on the structure of part (a) of FIG. 4. In one embodiment, the protective film 406 is formed by deposition and patterning of the material layer of the protective film 406. In one embodiment, subsequent to deposition of the protective film material, the combination of the bottom electrode and the protective film can be defined via lift-off or etching procedures. In the case that the protective film is a dielectric, the bottom electrode can be patterned and then the dielectric protective film can subsequently be deposited without any further patterning.

Referring to part (c) of FIG. 4, a sacrificial layer 408 is formed on the structure of part (b) of FIG. 4. In one embodiment, the sacrificial layer 408 is formed by a deposition and patterning approach. In one embodiment, the sacrificial layer 408 is composed of a material such as, but not limited to, Cr, W or Ti and has a thickness of approximately 100 nm or less. In one embodiment, the sacrificial layer 408 is formed by a deposition technique such as, but not limited to, sputtering, evaporation or ALD, and is patterned by lift-off or etching (wet or dry) techniques. In a specific embodiment, the ALD approach enables highly conformal coatings with high degree of thickness control, enabling very thin (e.g., less than 100 Angstroms) nanogaps which can further improve device sensitivity and minimize thinning/opening on potentially high aspect ratio electrode structures to provide devices with higher reliability (fabrication yield).

Referring to part (d) of FIG. 4, a top electrode 410 and corresponding protection layer 412 are formed on the structure of part (c) of FIG. 4. In one embodiment, the protective layer 412 is deposited first is a manner similar to formation of protection layer 406. The top electrode 410 material is then deposited and the combination of top electrode and protective layer can be patterned via lift-off or etching (dry/wet) techniques. In the case of the protective film being a dielectric, the protective film 412 does not need to be patterned, although it is shown as patterned in FIG. 4.

Referring to part (e) of FIG. 4, a passivation layer 414 is formed on the structure of part (d) of FIG. 4. In one embodiment, after the deposition and patterning of the top electrode (e.g., patterning is performed to leave an opening to access the sacrificial layer and the gap), a passivation dielectric 414 is deposited to minimize background current during measurement. In an exemplary embodiment, the passivation layer 414 is a layer of Plasma enhanced chemical vapor deposition (PECVD) Nitride/Oxide/Nitride (2300 A/3000 A/2300 A). Other dielectric layers such as SiC(O/N) or polymer layers such as polyimide can be used as a passivation layer given that the process is optimized to ensure the long term reliability/stability of the passivation layer and minimal leakage of current in the buffer fluid. Referring to part (f) of FIG. 4, the sacrificial layer 408 is then etched away using an appropriate selective wet etch to generate the nanogap geometry.

It is to be appreciated that other process fabrication schemes can also be pursued such as the deposition of a stack making up the layers all at once (e.g., bottom electrode/protective coating/sacrificial layer/protective coating/top electrode) and patterned via lift-off or etching (e.g., dry/wet) followed by subsequent top electrode contact definition and passivation. Although devices presented herein were, in accordance with one embodiment, fabricated using plain silicon substrates, the process can be repeated on planarized CMOS wafers for monolithic integration of the transducers with electronics.

Figure 5:
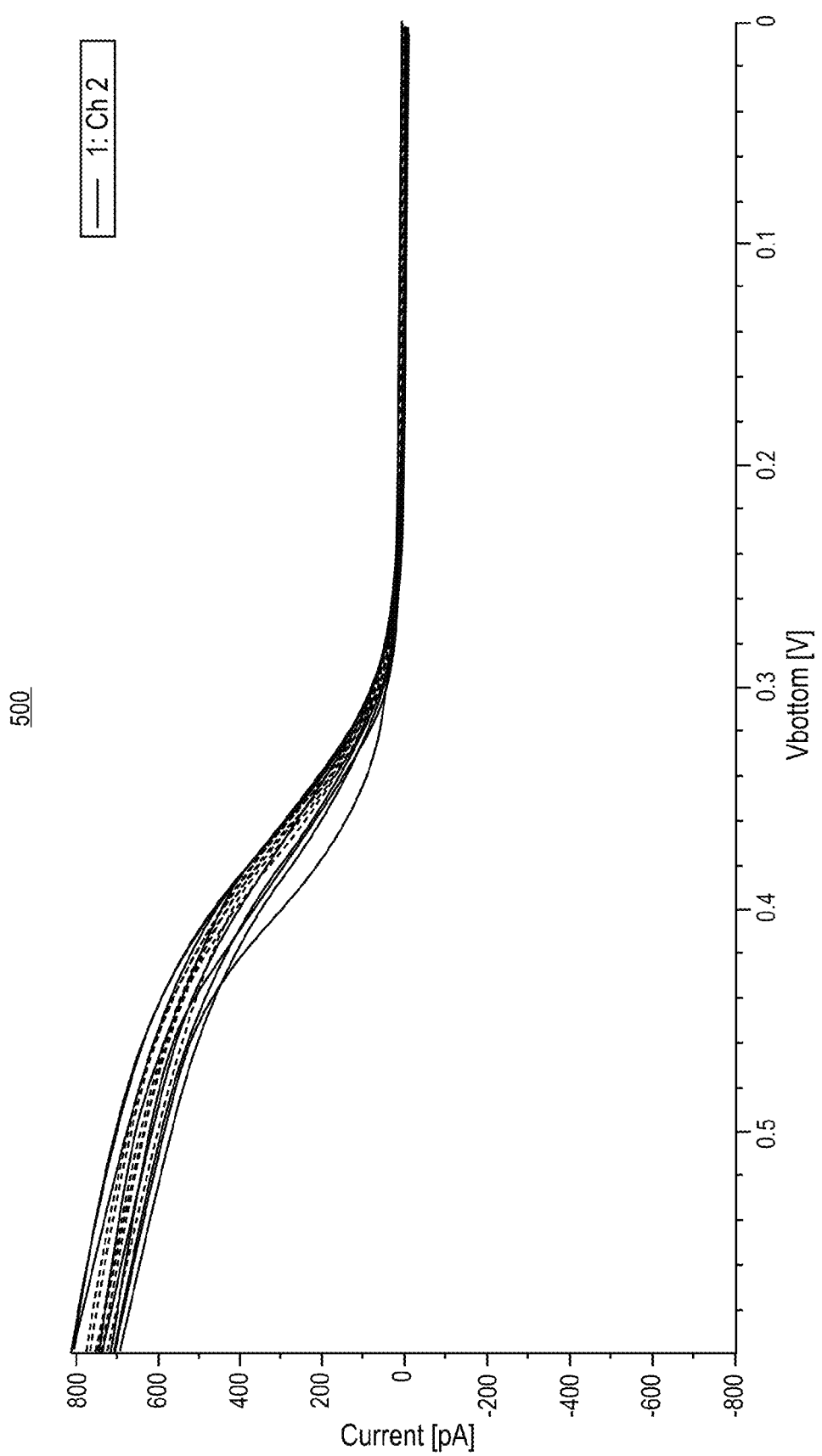
FIG. 5 depicts several cyclic voltammetry plots for a Pt-Pt nanogap device with 3 nm $TiO_2$ coatings using a model compound (10 uM Ferroscene) of redox potential at about 0.240V, in accordance with an embodiment of the present invention.

FIG. 5 is a plot 500 of cyclic voltammetry plots for a Pt-Pt nanogap device with 3 nm $TiO_2$ coatings using a model compound (10 uM Ferrocene) with a redox potential at about 0.240V, in accordance with an embodiment of the present invention. Referring to FIG. 5, cyclic voltammetry plots obtained with nanogap devices made of Pt electrodes and protected using $TiO_2$ films deposited using ALD reveal the superior electrochemical properties of such devices due to the reduced fouling effect.

In a second aspect, in accordance with another embodiment of the present invention, organic surface modified, i.e., coated, electrode nanogap transducers suitable for redox-based biochemical chemical sensing are described. One or more embodiments are directed to electrode surface modification processes and chemistry approaches additional to (i.e., in place of or in combination with) the above described protective film coated electrode nanogap transducers for the detection of redox molecules.

To provide context, sensitivity and specificity to detect biomolecules and chemicals at ultra-low concentrations has the potential to revolutionize several fields including clinical diagnostics, epidemic disease control, environmental monitoring, and food safety. Manufacturing electronic biomolecule and chemical sensors with scalability and speed enables the realization of highly affordable, customizable, and miniaturized systems for such applications including state-of-the-art DNA sequencing platforms.

One or more embodiments are directed to coating a transducer electrode material (e.g., platinum or other electrochemically active material such as diamond, gold, ITO, iridium oxide, etc.) with a well-defined or self-assembled monolayer or with very thin multiple layers of hydrophilic and biocompatible organic compounds (e.g.: polyethylene glycols, anilines, phosphonates, thiols, peptides, etc.), to reduce or prevent entirely catalytic reaction of the transducer material with the solution and or solution additives and reduce adsorption of the redox tags, without significantly reducing the electron transfer at the reducing and oxidizing electrodes. In one such embodiment, the organic or biomolecular coating possesses a low energy barrier to enable electron tunneling or hopping through or over the energy barrier to maintain a similar (e.g., 90 to 100%) electron transfer rate as with bare electrodes. In a specific embodiment, the coating is non-catalytic and non-electrochemically active (or with reduced catalytic and electrochemical activity) and can also be used as a protective film to reduce fouling or denaturing during analysis.

To provide context, the microstructure, cleanliness and chemical composition of an electrode surface in part determines how an electron-transfer reaction proceeds. Embodiments described herein include a method to protect an electrode surface from contamination by coating. The contact angle of a water droplet against a surface is a measure of the surface hydrophilicity. Experiments performed on clean platinum and gold have both demonstrated a hydrophilic nature. However, within only minutes of exposure to ambient laboratory conditions, both surfaces become increasingly hydrophobic. This change is attributed to adsorption or non-specific binding of various chemical species to the metal surfaces, indicating surface contamination.

One or more embodiments are directed to approaches for reliably fabricating a redox cycling sensor in a CMOS compatible manner, allowing dense integration on a single platform. The resulting devices may be, in an embodiment, similar to existing nanogap devices with the added feature of a coating of a well-defined or self-assembled monolayer or very thin multiple layers of hydrophilic and biocompatible organic compounds on both the bottom and top electrode material. The coating can be utilized to maximize the signal to noise ratio and to reduce fouling from occurring for the detection of any molecule that can go through reversible (or quasi reversible: depending on the detection scheme short lifetime reactions can also be detected) redox reactions. The same or similar coating scheme can also be used for transducers that possess one electrode (excluding a reference electrode if used) whereby cycling is accomplished chemically instead of electrically, as in the case of a nanogap transducer scheme.

In accordance with an embodiment of the present invention, in the case of DNA sequencing, a biochemical assay system (reaction) has been designed so that redox tags, that can be base specific, are generated close to or between two electrodes separated by a nanogap (e.g., 100 nm or less). A third reference electrode may be used to fix the bias of the fluid. The presence of the redox tags are detected by monitoring either one of the two or both electrode currents. Monitoring both electrodes permits detection of anti-correlated currents associated with the two electrodes when very small numbers of redox tags are present in the nanogap. Having two closely spaced electrodes biased close to the reduction and oxidation potentials of the redox tag allows signal amplification because the same molecule carries electrons from the oxidation electrode to the reduction electrode through the gap between these electrodes multiple times. Placing the electrodes closer to one another can result in higher signal since the increased proximity decreases the diffusion time of the redox tag from one electrode to another. The amount of current registered is proportional to the number of non-adsorbed molecules in the gap. In an embodiment, coating the electrode material with a well-defined or self-assembled monolayer or with very thin multiple layers of hydrophilic and biocompatible organic compounds in such a nanogap redox cycling architecture enables achievement of higher signal to noise ratio and prevents the occurrence of fouling. In a specific embodiment, the result allows corresponding readout circuitry to discriminate the redox current due to the redox label with minimum background current contribution from the buffer. The outcome may also be to present an inert surface, minimizing adsorption of molecules such that the same molecule can shuttle more electrons resulting in more signal. The design uses a minimum number of fabrication steps, decreasing the manufacturing cost and improving the yield.

One or more embodiments involve coating and thus protecting the transducer electrode material (e.g., platinum or another electrochemically active material such as diamond, gold, ITO, iridium oxide, etc) with a well-defined or self-assembled monolayer or with very thin multiple layers of hydrophilic organic polymer or biopolymers. In one embodiment, the coating is suitable to prevent (or at least substantially inhibit) catalytic reaction of the transducer material with solution additives and reduce the effect of adsorbed species, without affecting the electron transfer at the reducing and oxidizing electrodes. The coating layers can also be controlled with certain charge density to enhance electron transfer rate compared to bare electrodes. In one embodiment, the coatings are non-catalytic and non-electrochemically active (or with reduced catalytic and electrochemical activity) and can also be used as protective films to reduce fouling and denaturing. By changing the coating structure and charge properties, the electron transfer can be enhanced to improve the sensitivity. By doing so, previous solutions may not be needed, reducing complexity, increasing yield and producing reliable and repeatable results. Moreover, embodiments described herein can provide the option to operate at a wider variety of electrode potentials, increasing the options for redox tags that allows for the optimization of the tag molecules for maximum signal. In addition, the developed process may be scalable such that semiconductor manufacturing scalability may be used to reduce the size of the sensor.

Figure 6:
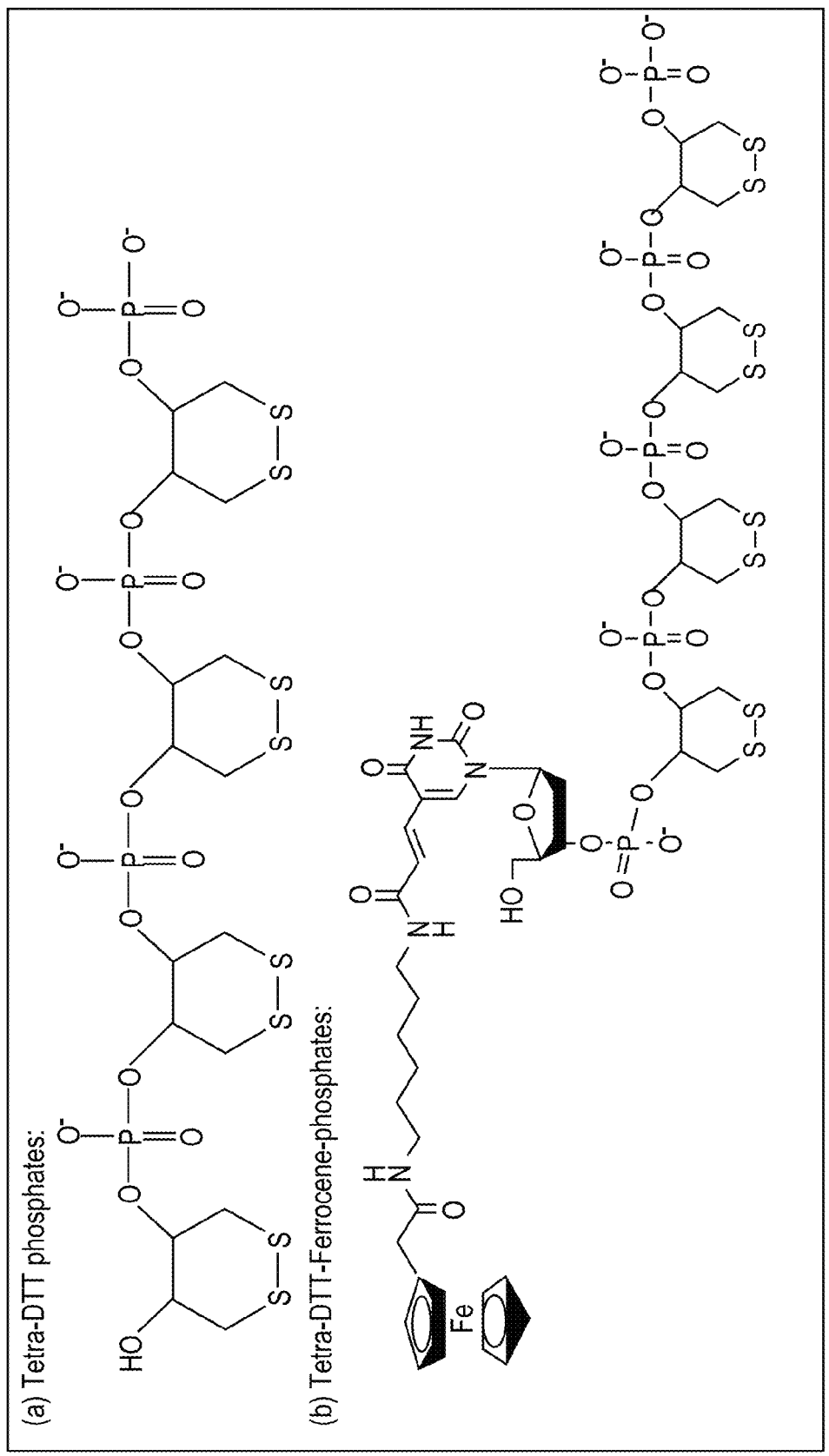
FIG. 6 illustrates examples of organic molecules suitable for electrode coating, in accordance with an embodiment of the present invention.

FIG. 6 illustrates examples of organic molecules suitable for electrode coating, in accordance with an embodiment of the present invention. Referring to part (a) of FIG. 6, tetra-DTT phosphates may be used as a surface coating molecule. Referring to part (b) of FIG. 6, tetra-DTT-ferrocene phosphates may be used as a surface coating molecule. These examples may be included on an electrode surface by a fabrication process suitable to incorporate the protective organic coating, such as processes described herein. Applications include usage of a resulting transducer for DNA sequencing or for enzymatically tagged assays.

In an embodiment, a unique combination of incorporating protective organic coatings on electrodes with a nanogap architecture for redox cycling detection of molecules is achieved. The fabrication process flow may be viewed as having five main considerations (and variations thereof) which are outlined below.

In a first consideration, in an embodiment, formation of the bottom electrode involves formation of the bottom electrode (e.g., as a deposited material) with minimum surface roughness and with minimum thickness in order to minimize the probability of shorting of the top and bottom electrodes. Roughness may cause openings in a corresponding sacrificial conformal coating and the edges with high aspect ratios may cause thinning or voids in the sacrificial layer. In one such embodiment, the bottom electrode (e.g., platinum, gold, diamond, ITO, iridium oxide, etc.) is deposited with a suitable technique (e.g., evaporation, sputtering, ALD, CVD, hot filament, etc.). In the case that thick films are required for deposition (e.g. diamond), high aspect ratio structures at the edges of the electrodes are created. The high aspect ratio structures can cause thinning of the sacrificial film at the edges of the electrodes, increasing the probability of shorting between the top and bottom electrodes. To mitigate this problem, in one embodiment, the nanogap devices are planarized by depositing a dielectric layer (e.g., silicon nitride or silicon dioxide) and using chemical mechanical polishing (CMP) of the dielectric to achieve a planar surface for enhanced conformal coating of the following layers.

In a second consideration, regarding formation of the sacrificial film, in an embodiment, a sacrificial layer (e.g., Cr, W, Ti, etc) that is approximately 500 Angstroms in thickness or less, is deposited (by sputtering, evaporation, ALD, etc.) and patterned by lift-off or an etching (wet or dry) approach. The ALD technique can enable highly conformal coatings with a high degree of thickness control, enabling very thin (e.g., less than approximately 100 Angstroms) nanogaps which will further improve device sensitivity and minimal thinning/opening on potentially high aspect ratio electrode structures to provide devices with higher reliability.

In a third consideration, regarding formation of the top electrode, in an embodiment, the top electrode material is deposited and the combination of top electrode and protective layer is patterned via lift-off or etching (dry/wet) techniques.

In a fourth consideration, regarding passivation of the nanogap devices, in an embodiment, subsequent to deposition and patterning of the top electrode (e.g., patterning is performed to leave an opening to access the sacrificial layer and the gap), a passivation dielectric is deposited to minimize background current during measurement. In an exemplary embodiment, a layer of plasma enhanced chemical vapor deposition (PECVD) Nitride/Oxide/Nitride (2300 A/3000 A/2300 A) is used as a passivation layer. Other dielectric layers such as SiC(O/N) or polymer layers such as polyimide can be used as a passivation layer given that the process is optimized to ensure the long term reliability/stability of the passivation layer and minimal leakage of current in the buffer fluid. The sacrificial layer may then be etched away in the appropriate selective wet bath to create the nanogap geometry.

In a fifth consideration, regarding surface coating, in an embodiment, other processes can also be implemented such as the deposition of a stack making up the layers all at once (e.g., bottom electrode/protective coating/sacrificial layer/protective coating/top electrode) and patterned via lift-off or etching (dry/wet) followed by subsequent top electrode contact definition and passivation.

In an embodiment, applying the organic material coating is performed by physical absorption, chemical bonding and/or by electroplating. Although devices presented herein may be contemplated as fabricated using plain silicon substrates, the process can also be implemented on planarized CMOS wafers for monolithic integration of the transducers with electronics.

Figure 7:
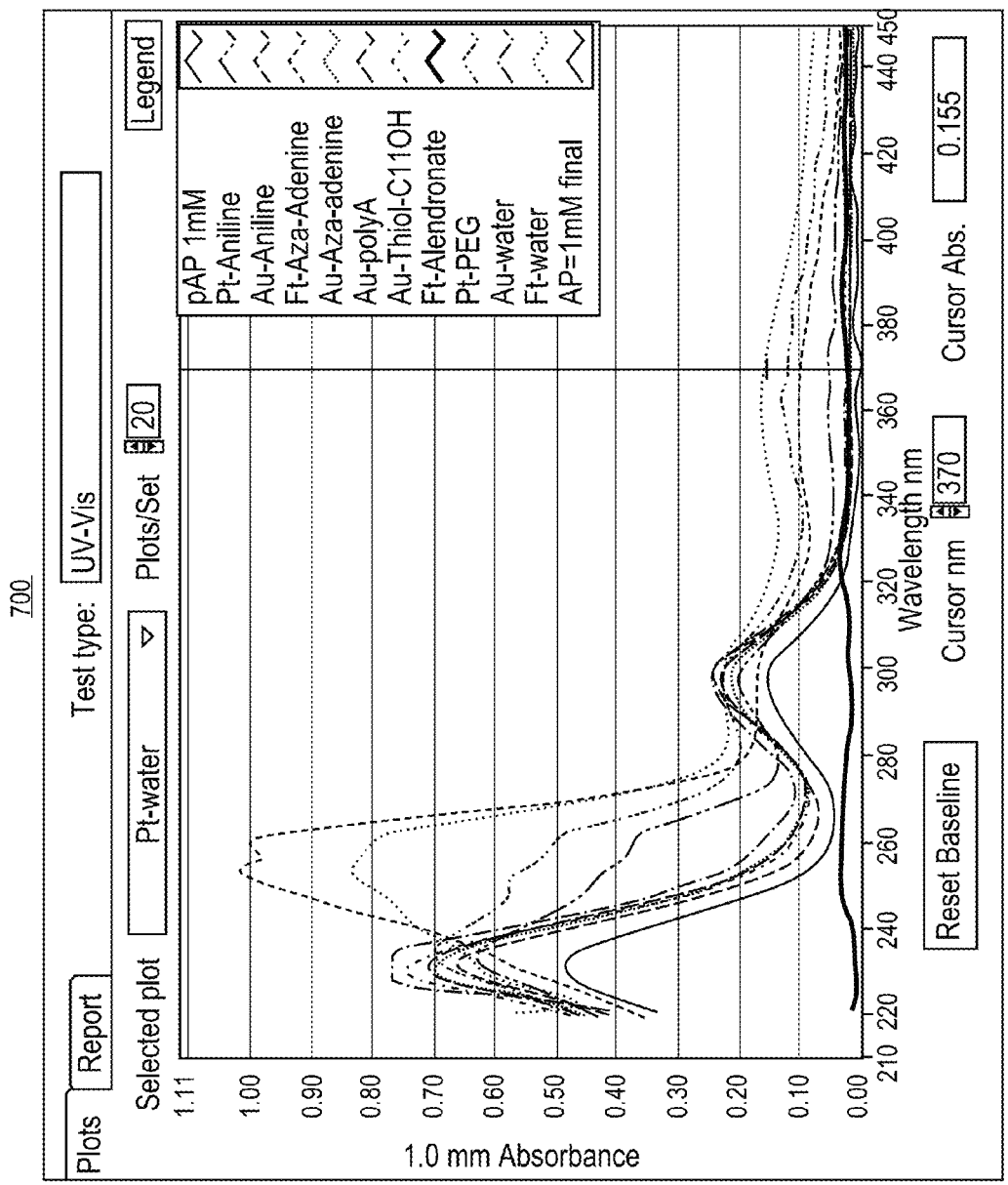
FIG. 7 is a plot demonstrating UV-Vis monitoring of a redox active molecule aminophenol on coated electrode compared with bare electrode, in accordance with an embodiment of the present invention.

FIG. 7 is a plot 700 demonstrating UV-Vis monitoring of a redox active molecule aminophenol on coated electrode compared with bare electrode, in accordance with an embodiment of the present invention. Referring to plot 700, the red-shifting from 238 nm to 260 nm and from 300 nm to 370 nm indicates the catalytical oxidation of aminophenol. The organic coating minimized the catalytical activity of the electrode Pt surface. Among the coatings (e.g., aniline, aza-adenine, poly-adenosine (polyA), mercaptoundecanol (Thiol-C11OH), and polyethylene glycol (PEG)), the aniline rendered most effective protection, in a particular embodiment.

FIG. 8 illustrates alendronate derivatives suitable for organic coatings, in accordance with an embodiment of the present invention. Referring to FIG. 8, exemplary structures are shown for positive derivatives 802, neutral derivatives 804, negative derivatives 806, and mediating derivatives 808.

Figure 9:
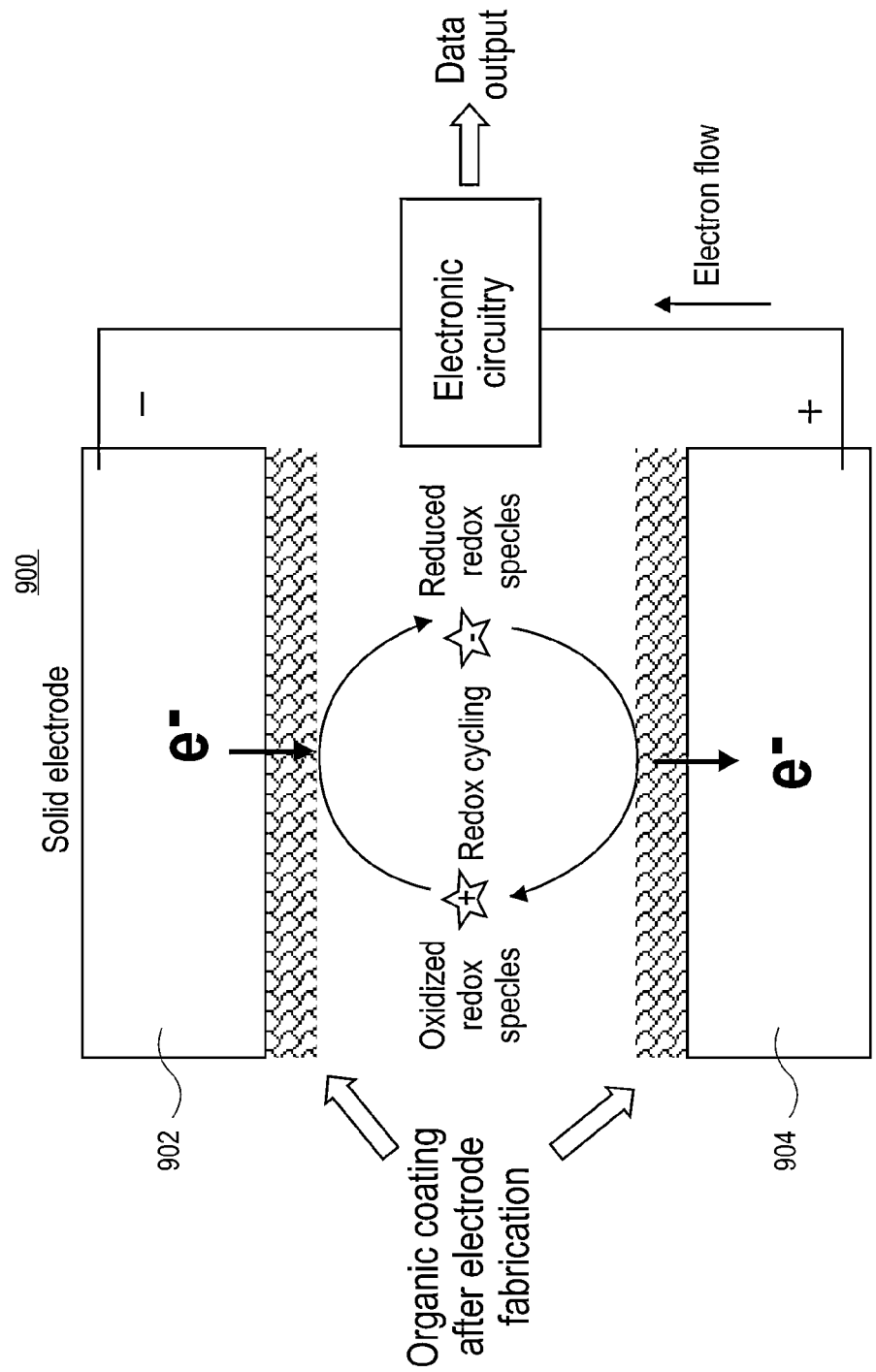
FIG. 9 illustrates a schematic of a nanogap transducer device with protective coatings, in accordance with an embodiment of the present invention.

FIG. 9 illustrates a schematic of a nanogap transducer device 900 with protective coatings, in accordance with an embodiment of the present invention. Referring to FIG. 9, solid electrodes are shown as organic-coated nanogap electrodes 902 and 904. In one embodiment, the organic coating is applies subsequent to electrode fabrication, as depicted.

Figure 10:
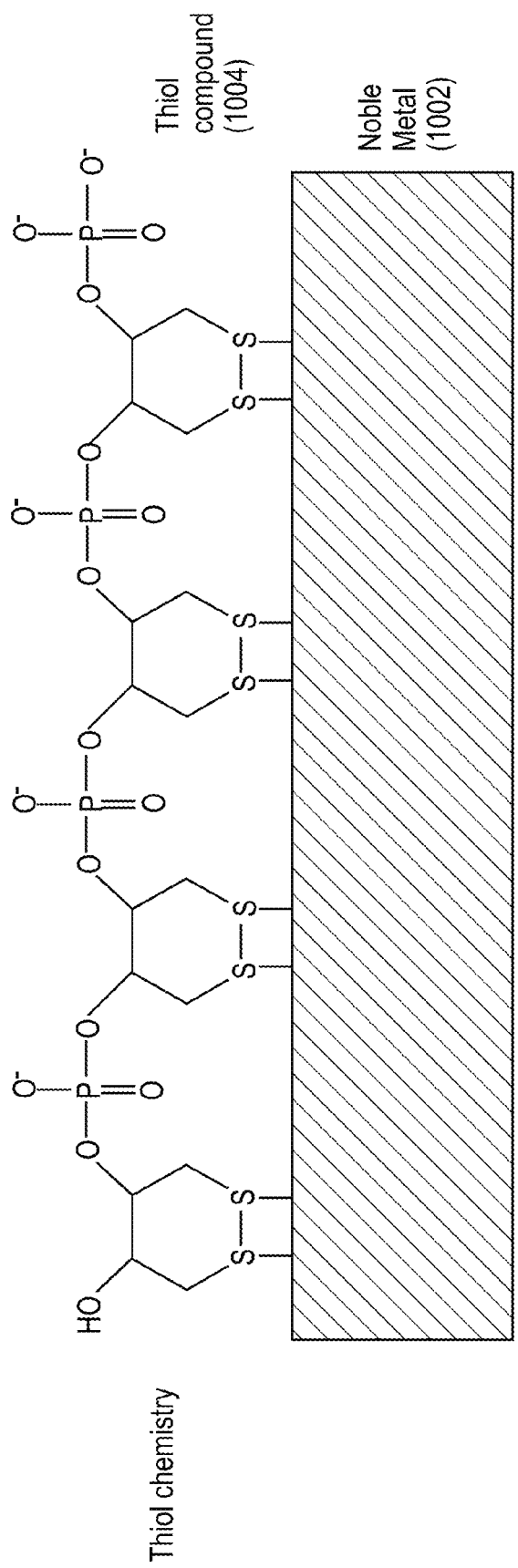
FIG. 10 illustrates an organic coated metal electrode surface along with suitable molecular coatings, in accordance with an embodiment of the present invention.
Figure 10:
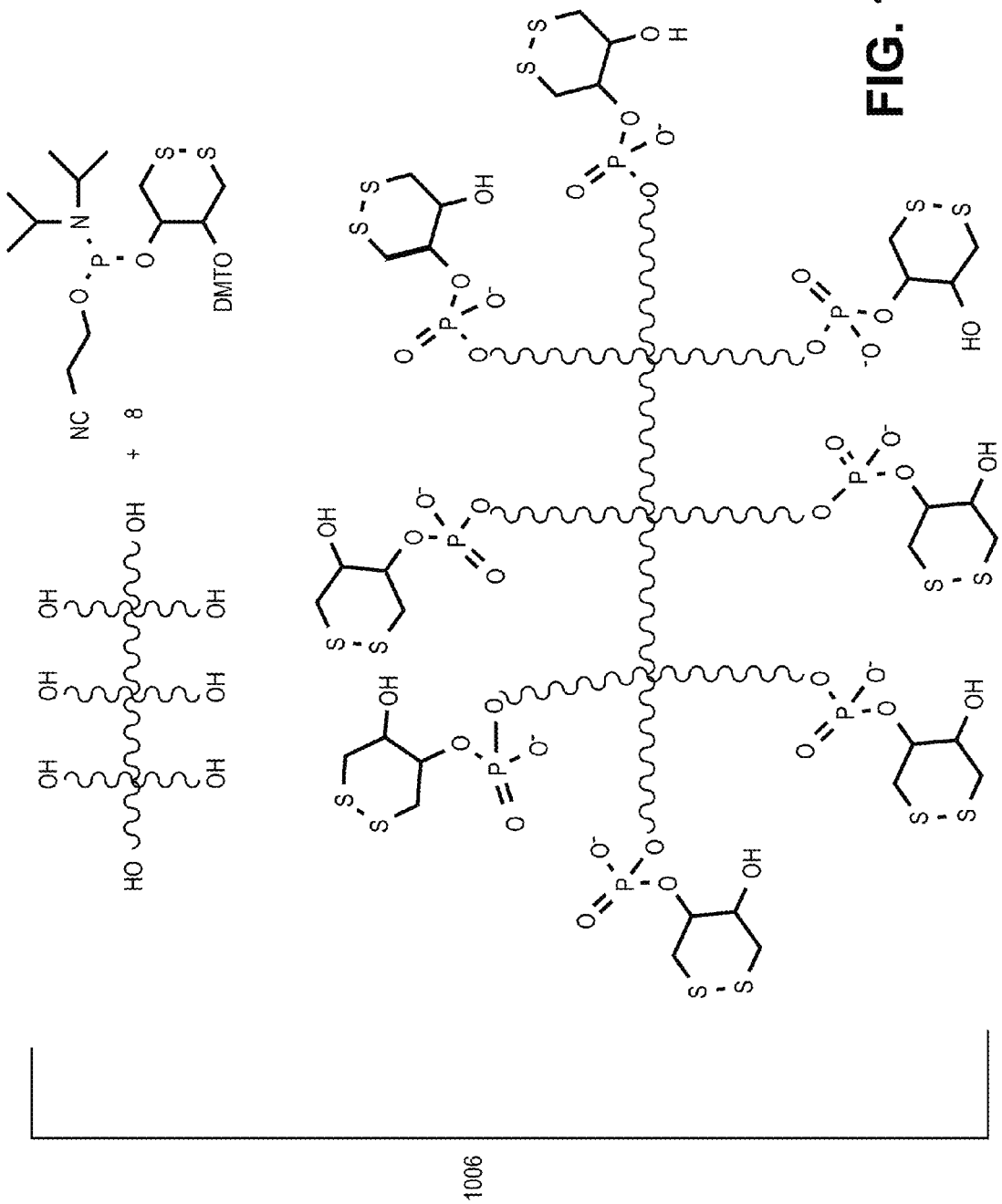
Figure 10:
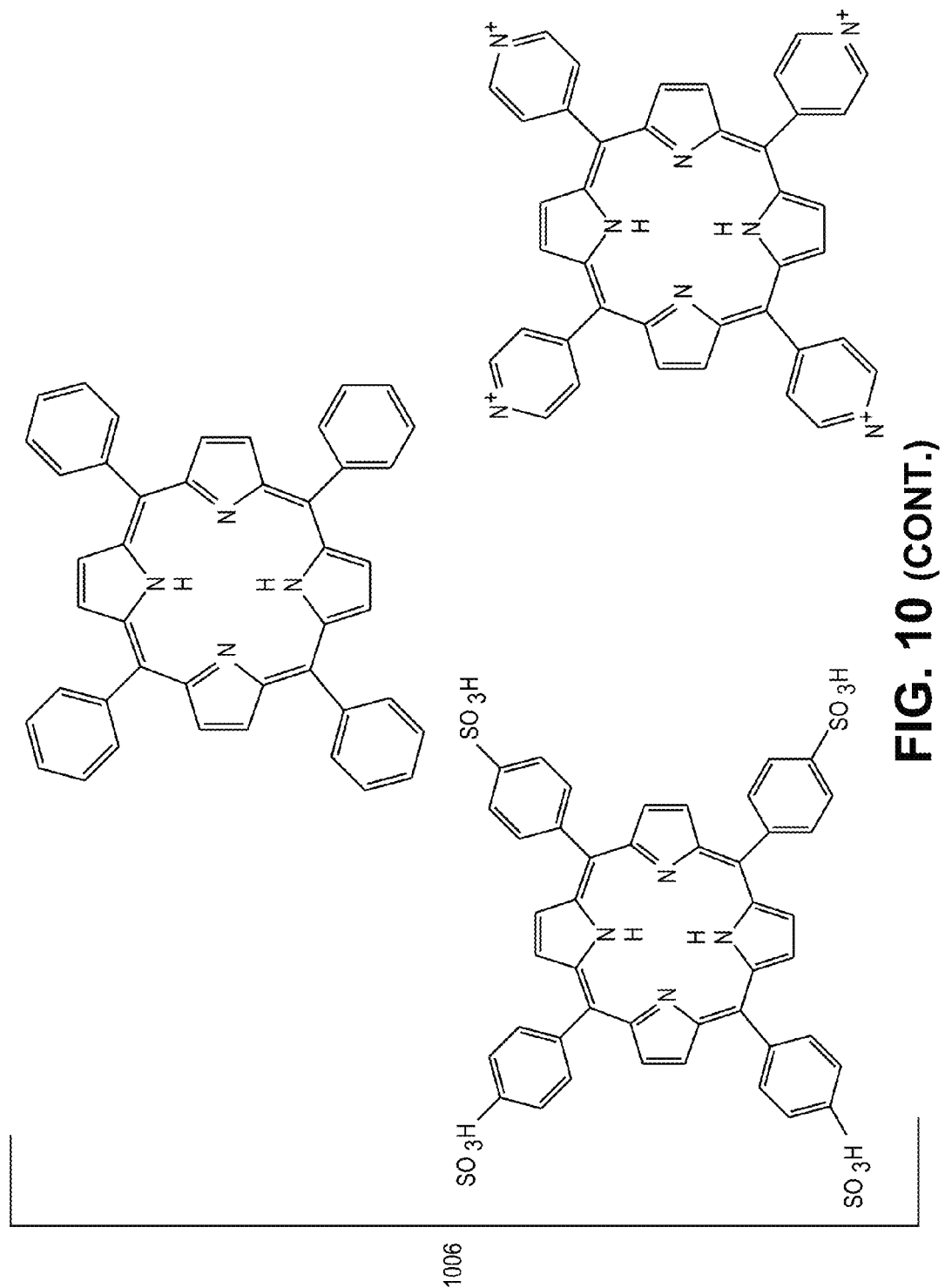

FIG. 10 illustrates an organic coated metal electrode surface along with suitable molecular coatings, in accordance with an embodiment of the present invention. Referring to FIG. 10, a noble metal electrode 1002 has thereon a thiol compound-based surface coating 1004. The grouping of exemplary molecules 1006 provide additional examples of suitable surface coating molecules.

Figure 11:
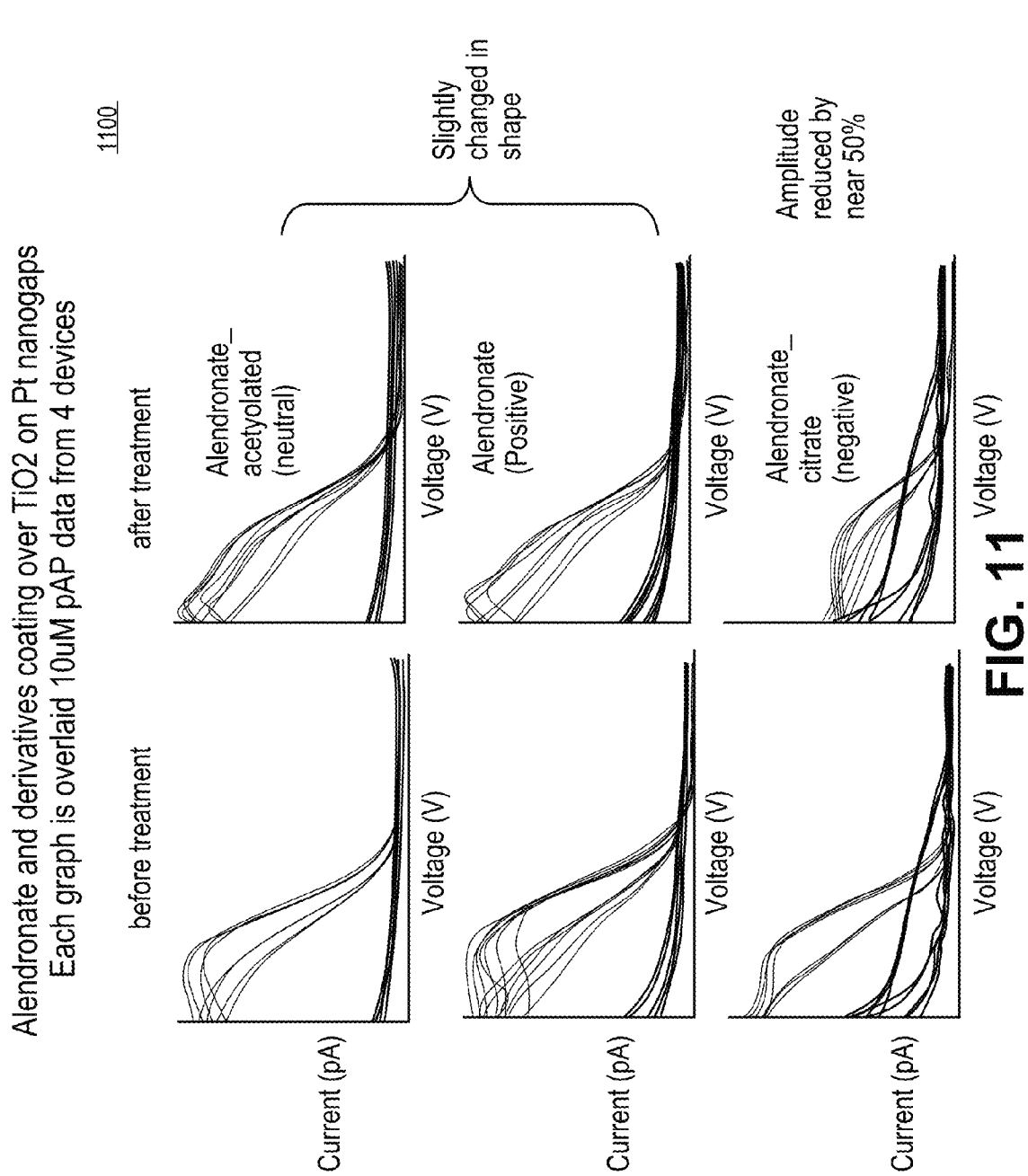
FIG. 11 includes a plurality of CV scans of coated nanogap devices, in accordance with embodiments of the present invention.
Figure 12:
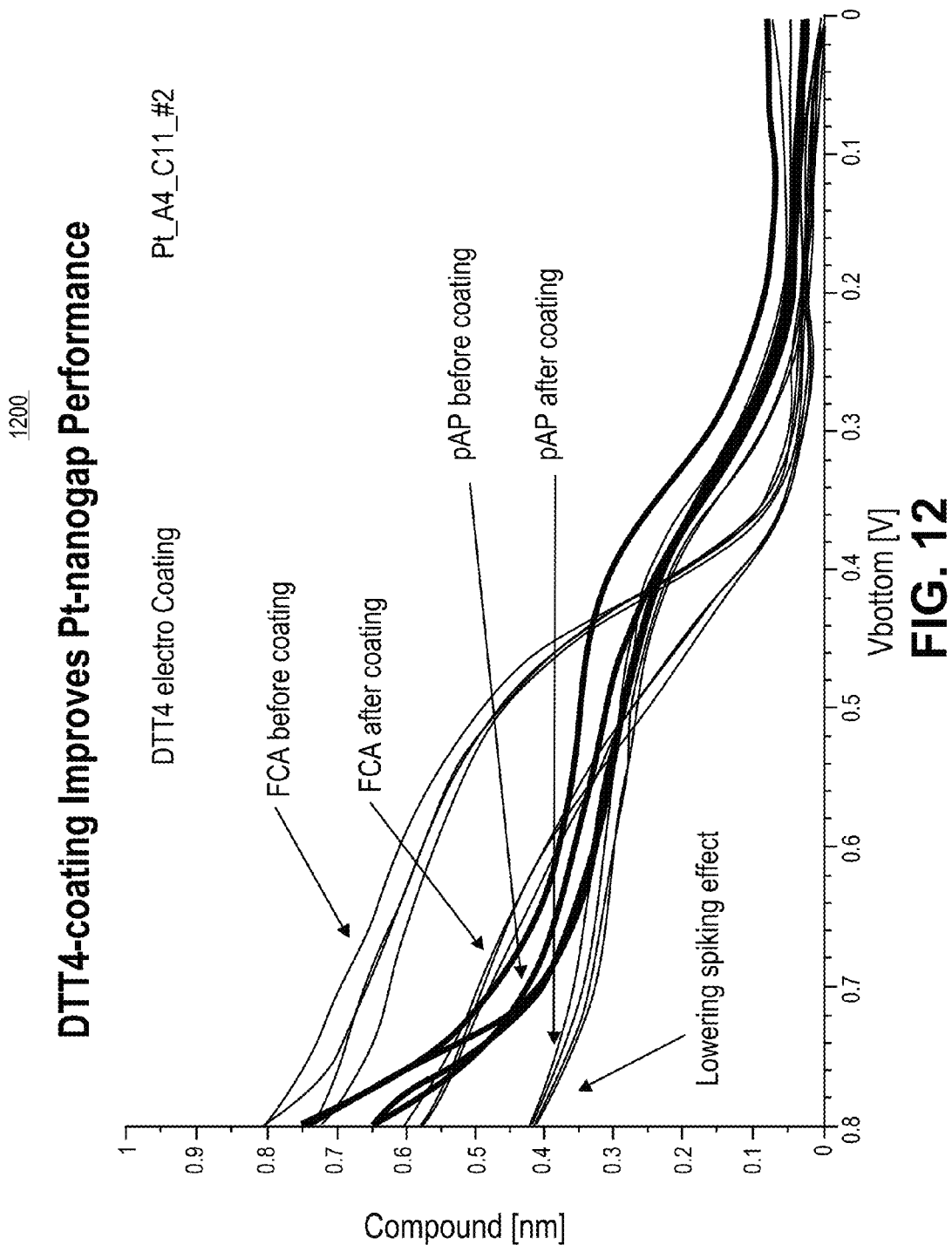
FIG. 12 is a plot demonstrating the effects of a DTT4 coating on a Pt nanogap, in accordance with an embodiment of the present invention.

FIG. 11 includes a plurality of CV scans 1100 of coated nanogap devices, in accordance with an embodiment of the present invention. Referring to FIG. 11, alendronate and derivatives coating over $TiO_2$ on Pt nanogaps is demonstrated where each graph of 1100 is overlaid 10 uM pAP data from four devices. Additionally, FIG. 12 is a plot 1200 demonstrating the DTT4 coating effect on a Pt nanogap, in accordance with an embodiment of the present invention.

For all aspects described above, in an embodiment, the resulting devices can be utilized for fabricating an ultra dense array of chemically modified sensors on a silicon platform for whole genome sequencing. In one such embodiment, each sensor is used to detect the chemical signal generated (e.g., in the form of a redox active molecule) from the test/fill reaction at a specific location, identifying the base pair. These devices may be crucial in sensing signaling molecules being produced at each location. However the above described usage is not so limited. For example, in another embodiment, electrodes having coatings as described above provide an enabling technology for the densely integrated transducer array through sensitive and robust detection of base specific redox tags. Improving the signal to noise ratio of the transducers allows the detection with higher confidence and also relaxes the requirements on the associated biochemistry. In general, embodiments described herein may be suitable for a variety of implementations involving high sensitivity electronic biosensor array-based applications. Applications can range from having the redox active species as analytes in a solution or using the redox active molecule as a label for the detection of some primary specie as done in our case. Some examples of applications in which redox actives species may play a role can be in high throughput DNA sequencing, biomolecule detection for disease monitoring, point of care diagnostics.

To provide another general context, overall, one or more embodiments are directed to performing redox detection, such as DNA sequencing, based on electrical signal detection. An integrated electronic circuit can be used to detect such signals. The combination of the chemistry scheme with CMOS integrated circuits (ICs) and sequencing applications provides advantages not previously realized in conventional detection approaches. Furthermore, CMOS IC chips can be used for massive human genome sequence information generation, which can leverage advanced fabrication technology.

As used herein, "sensor" or "transducer" refers to a substance or device that detects or senses an electrical signal created by movement of electrons, including but not limited to electrical resistance, current, voltage and capacitance. That is, the transducer or sensor can detect signals in the form of current, or detect voltage, or detect charge, or impedance or magnetic field, or a combination thereof. A transducer array has one or more transducers, up to billions of transducers.

An "array" is an intentionally created collection of substances, such as molecules, openings, microcoils, detectors and/or sensors (or transducers), attached to or fabricated on a substrate or solid surface, such as glass, plastic, silicon-chip, IC chip or other material forming an array. The arrays (such as sensor/transducer arrays) can be used to measure the signal locations and levels of large numbers, e.g., tens, thousands, millions, or billions of reactions or combinations simultaneously. An array may also contain a small number of substances, e.g., a few or a dozen. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads (features) on the array. A macroarray generally contains pad (feature) sizes of about 300 microns or as small as 1 micron, or even 0.1 micron. A sensor array would generally contain pad sizes of less than 300 microns. Sensing elements (e.g., sensor array features or sensor pads) of the sensor/transducer array can be electronically individually addressable.

The term "analyte" refers to a molecule of interest that is to be detected and/or analyzed, e.g., a nucleotide, an oligonucleotide, a polynucleotide, a peptide, or a protein. The analyte, target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be a fluorescently labeled antigen, antibody, DNA or RNA. A "bioanalyte" refers to an analyte that is a biomolecule. Specifically, analytes for DNA sequencing can be samples containing nucleic acid molecules, such as genomic or synthetic, or biochemically amplified DNA or cDNA. "Analyte" molecule can be used interchangeably with "target" molecule.

The term "tag" is used to refer to a marker or indicator distinguishable by the observer but not necessarily by the system used to identify an analyte or target. A tag may also achieve its effect by undergoing a pre-designed detectable process. Tags are often used in biological assays to be conjugated with, or attached to, an otherwise difficult to detect substance. At the same time, tags usually do not change or affect the underlining assay process. A tag used in biological assays include, but not limited to, a radio-active material, a magnetic material, quantum dot, an enzyme, a liposome-based label, a chromophore, a fluorophore, a dye, a nanoparticle, a quantum dot or quantum well, a composite-organic-inorganic nano-cluster, a colloidal metal particle, or a combination thereof. In one embodiment, a tag or a label is preferably a metal-organic complex that can be induced to generate electron current upon light exposure.

Figure 13:
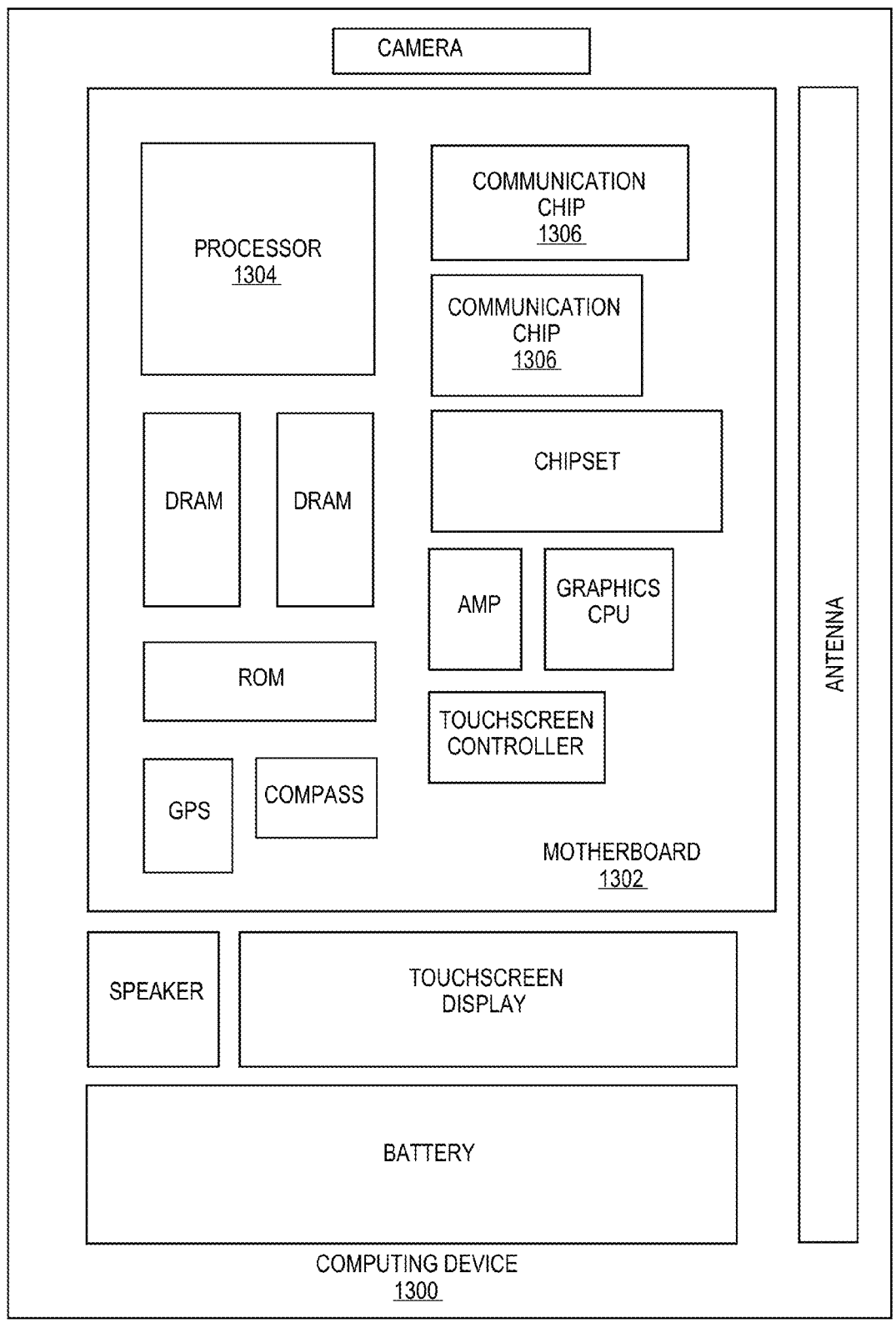
FIG. 13 illustrates a computing device in accordance with one implementation of the invention.

FIG. 13 illustrates a computing device 1300 in accordance with one implementation of the invention. The computing device 1300 houses a board 1302. The board 1302 may include a number of components, including but not limited to a processor 1304 and at least one communication chip 1306. The processor 1304 is physically and electrically coupled to the board 1302. In some implementations the at least one communication chip 1306 is also physically and electrically coupled to the board 1302. In further implementations, the communication chip 1306 is part of the processor 1304.

Depending on its applications, computing device 1300 may include other components that may or may not be physically and electrically coupled to the board 1302. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

The communication chip 1306 enables wireless communications for the transfer of data to and from the computing device 1300. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 1306 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. The computing device 1300 may include a plurality of communication chips 1306. For instance, a first communication chip 1306 may be dedicated to shorter range wireless communications such as Wi-Fi and Bluetooth and a second communication chip 1306 may be dedicated to longer range wireless communications such as GPS, EDGE, GPRS, CDMA, WiMAX, LTE, Ev-DO, and others.

The processor 1304 of the computing device 1300 includes an integrated circuit die packaged within the processor 1304. In some implementations of the invention, the integrated circuit die of the processor includes or is coupled to an integrated transducer array, in accordance with implementations of the invention. The term "processor" may refer to any device or portion of a device that processes electronic data from registers and/or memory to transform that electronic data into other electronic data that may be stored in registers and/or memory.

The communication chip 1306 also includes an integrated circuit die packaged within the communication chip 1306. In accordance with another implementation of the invention, the integrated circuit die of the communication chip includes or is coupled with an integrated transducer array in accordance with implementations of the invention.

In further implementations, another component housed within the computing device 1300 may contain an integrated circuit die that includes or is coupled with an integrated transducer array in accordance with implementations of the invention.

In various implementations, the computing device 1300 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, the computing device 1300 may be any other electronic device that processes data.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 14:
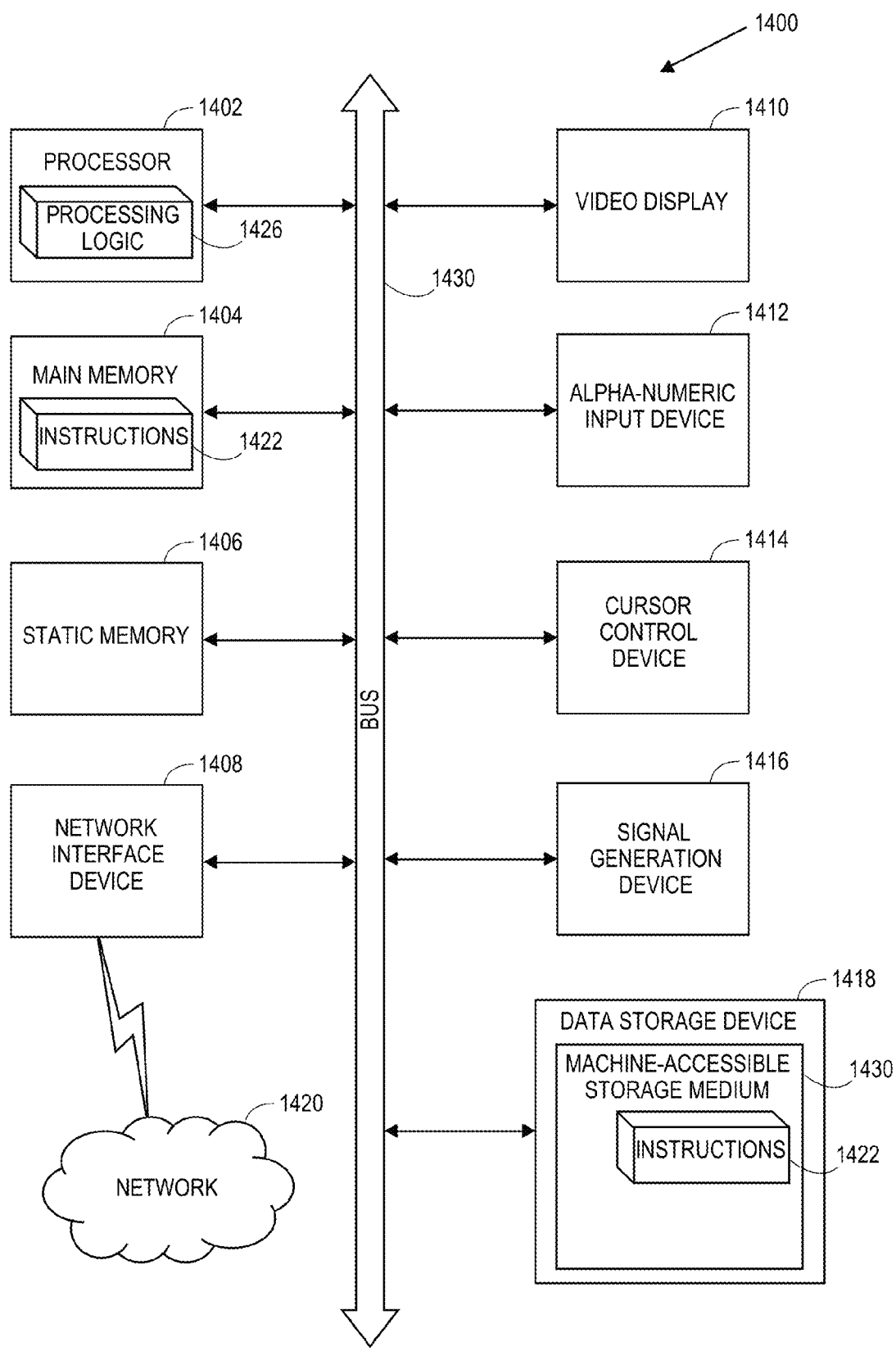
FIG. 14 illustrates a block diagram of an exemplary computer system, in accordance with an embodiment of the present invention.

FIG. 14 illustrates a diagrammatic representation of a machine in the exemplary form of a computer system 1400 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1400 includes a processor 1402, a main memory 1404 (e.g., read-only memory (ROM), flash memory, dynamic random access memory (DRAM) such as synchronous DRAM (SDRAM) or Rambus DRAM (RDRAM), etc.), a static memory 1406 (e.g., flash memory, static random access memory (SRAM), etc.), and a secondary memory 1418 (e.g., a data storage device), which communicate with each other via a bus 1430.

Processor 1402 represents one or more general-purpose processing devices such as a microprocessor, central processing unit, or the like. More particularly, the processor 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1402 may also be one or more special-purpose processing devices such as an application specific integrated circuit (ASIC), a field programmable gate array (FPGA), a digital signal processor (DSP), network processor, or the like. Processor 1402 is configured to execute the processing logic 1426 for performing the operations discussed herein.

The computer system 1400 may further include a network interface device 1408. The computer system 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1416 (e.g., a speaker).

The secondary memory 1418 may include a machine-accessible storage medium (or more specifically a computer-readable storage medium) 1431 on which is stored one or more sets of instructions (e.g., software 1422) embodying any one or more of the methodologies or functions described herein. The software 1422 may also reside, completely or at least partially, within the main memory 1404 and/or within the processor 1402 during execution thereof by the computer system 1400, the main memory 1404 and the processor 1402 also constituting machine-readable storage media. The software 1422 may further be transmitted or received over a network 1420 via the network interface device 1408.

While the machine-accessible storage medium 1431 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

Thus, embodiments of the present invention include highly selective coated-electrode nanogap transducers for the detection of redox molecules.

In an embodiment, an analyte detection system includes one or more transducer electrodes having a surface for analyte detection. The surface includes a coating to inhibit direct contact of analyte with the surface of the one or more transducer electrodes.

In one embodiment, the coating is composed of a dielectric film.

In one embodiment, the dielectric film is composed of a material such as, but not limited to, $Ta_2O_5$, $TiO_2$, $SiO_2$, $Y_2O_3$, $Al_2O_3$, $HfO_2$, $ZrO_2$, $ZrSiO_4$, $BaTiO_3$, $BaZrO_3$ or $Si_3N_4$.

In one embodiment, the dielectric film has a thickness approximately in the range of 0-7 nanometers.

In one embodiment, the dielectric film has a low energy barrier to enable electron tunneling or hopping through or over the energy barrier to maintain a similar electron transfer rate relative to a bare electrode.

In one embodiment, the coating is composed of a thin conductive material that is non-catalytic and non-electrochemically active.

In one embodiment, the thin conductive material is ruthenium (Ru).

In one embodiment, the coating is composed of an organic film.

In one embodiment, the organic film is composed of a well-defined or self-assembled monolayer or very thin multiple layers of hydrophilic and biocompatible organic compounds such as, but not limited to, polyethylene glycols, anilines, phosphonates, thiols or peptides.

In one embodiment, the organic film is composed of a tetra-DTT phosphate or a tetra-DTT-ferrocene phosphate.

In one embodiment, the organic film has a low energy barrier to enable electron tunneling or hopping through or over the energy barrier to maintain a similar electron transfer rate relative to a bare electrode.

In one embodiment, the one or more transducer electrodes is composed of a material such as, but not limited to, platinum, diamond, gold, indium tin oxide (ITO) or iridium oxide.

In one embodiment, the coating reduces or prevents catalytic reaction of the one or more transducer electrodes with solution additives and reduces the effect of adsorbed species without affecting the electron transfer at reducing and oxidizing electrodes.

In one embodiment, the one or more transducer electrodes are included in a dual-electrode nanogap chemical and biochemical sensor based on detection of a redox-active molecule using redox cycling.

In one embodiment, the analyte detection system includes only one transducer electrode are included in a single-electrode based on chemical cycling.

In an embodiment, a method of fabricating a dual-electrode nanogap chemical and biochemical sensor involves forming a bottom electrode above a substrate. The method also involves forming a first coating on the bottom electrode. The method also involves forming a sacrificial layer on the first coating. The method also involves forming a second coating on the sacrificial layer. The method also involves forming a top electrode on the second coating. The method also involves, subsequent to forming the second coating and the top electrode, removing the sacrificial layer without removing the first and second coatings.

In one embodiment, forming the first and second coatings involves forming a dielectric film.

In one embodiment, forming the dielectric film involves forming a material such as, but not limited to, $Ta_2O_5$, $TiO_2$, $SiO_2$, $Y_2O_3$, $Al_2O_3$, $HfO_2$, $ZrO_2$, $ZrSiO_4$, $BaTiO_3$, $BaZrO_3$ or $Si_3N_4$.

In one embodiment, forming the first and second coatings involves forming a thin conductive material that is non-catalytic and non-electrochemically active.

In one embodiment, forming the thin conductive material involves forming a ruthenium (Ru) layer.

In an embodiment, a method of fabricating an analyte detection system involves forming one or more bare transducer electrodes having a surface for analyte detection. The method also involves forming an organic film on the surface to inhibit direct contact of analyte with the surface of the one or more transducer electrodes.

In one embodiment, forming the organic film involves forming a well-defined or self-assembled monolayer or very thin multiple layers of hydrophilic and biocompatible organic compounds such as, but not limited to, polyethylene glycols, anilines, phosphonates, thiols or peptides.

In one embodiment, forming the organic film involves forming a film of a tetra-DTT phosphate or of a tetra-DTT-ferrocene phosphate.

What is claimed is:

1. An analyte detection apparatus, comprising:
   one or more transducer electrodes having a surface for analyte detection, the surface comprising a coating to inhibit direct contact of analyte with the surface of the one or more transducer electrodes, wherein the coating comprises an organic film comprising a tetra-DTT phosphate or a tetra-DTT-ferrocene phosphate.

2. The analyte detection apparatus of claim 1, wherein the organic film has a low energy barrier to enable electron tunneling or hopping through or over the energy barrier to maintain a similar electron transfer rate relative to a bare electrode.

3. The analyte detection apparatus of claim 1, wherein the one or more transducer electrodes comprises a material selected from the group consisting of platinum, diamond, gold, indium tin oxide (ITO) and iridium oxide.

4. The analyte detection apparatus of claim 1, wherein the coating reduces or prevents catalytic reaction of the one or more transducer electrodes with solution additives and reduces the effect of adsorbed species without significantly affecting the electron transfer at reducing and oxidizing electrodes.

5. The analyte detection apparatus of claim 1, wherein the one or more transducer electrodes are included in a dual-electrode nanogap chemical and biochemical sensor based on detection of a redox-active molecule using redox cycling.

6. The analyte detection apparatus of claim 1, wherein the analyte detection system includes only one transducer electrode included in a single-electrode based on chemical cycling.

* * * * *